United States Patent
Beraja et al.

(10) Patent No.: US 8,392,213 B2
(45) Date of Patent: *Mar. 5, 2013

(54) MEDICAL CLAIMS FRAUD PREVENTION SYSTEM INCLUDING HISTORICAL PATIENT LOCATING FEATURE AND ASSOCIATED METHODS

(76) Inventors: Roberto Beraja, Coral Gables, FL (US); Victor Beraja, Coral Gables, FL (US); Esther Beraja, Coral Gables, FL (US); Isidoro Beraja, Coral Gables, FL (US); Matilde Beraja, Coral Gables, FL (US)

(*) Notice: Subject to any disclaimer, the term of this patent is extended or adjusted under 35 U.S.C. 154(b) by 232 days.

This patent is subject to a terminal disclaimer.

(21) Appl. No.: 12/832,500

(22) Filed: Jul. 8, 2010

(65) Prior Publication Data

US 2010/0274583 A1 Oct. 28, 2010

Related U.S. Application Data

(60) Continuation-in-part of application No. 12/614,841, filed on Nov. 9, 2009, which is a continuation-in-part of application No. 11/928,690, filed on Oct. 30, 2007, now Pat. No. 8,260,633, which is a division of application No. 11/191,304, filed on Jul. 28, 2005, now Pat. No. 7,464,042.

(51) Int. Cl.
*G06Q 50/00* (2012.01)
(52) U.S. Cl. ............................................. 705/2
(58) Field of Classification Search .......... 705/2, 16, 705/30; 235/382
See application file for complete search history.

(56) References Cited

U.S. PATENT DOCUMENTS

| | | | |
|---|---|---|---|
| 5,255,183 A * | 10/1993 | Katz ........................ 705/30 |
| 5,359,509 A | 10/1994 | Little et al. |
| 5,583,758 A | 12/1996 | McIlroy et al. |
| 5,924,073 A | 7/1999 | Tyuluman et al. |
| 5,924,074 A | 7/1999 | Evans |
| 5,946,659 A | 8/1999 | Lancelot et al. |
| 6,047,259 A | 4/2000 | Campbell et al. |
| 6,188,988 B1 | 2/2001 | Barry et al. |
| 6,283,761 B1 | 9/2001 | Joao |
| 6,341,265 B1 | 1/2002 | Provost et al. |
| 6,484,144 B2 | 11/2002 | Martin et al. |
| 6,684,276 B2 | 1/2004 | Walker et al. |
| 6,827,670 B1 | 12/2004 | Stark et al. |
| 6,988,088 B1 | 1/2006 | Miikkulainen et al. |
| 7,256,708 B2 | 8/2007 | Rosenfeld et al. |
| 7,421,399 B2 | 9/2008 | Kimmel |
| 2001/0012913 A1 | 8/2001 | Iliff |
| 2001/0034618 A1 | 10/2001 | Kessler et al. |
| 2002/0019749 A1 | 2/2002 | Becker et al. |

(Continued)

OTHER PUBLICATIONS

Medical Expert Systems, May 20, 2005. http://www.computer.privateweb.at/judith/name_3.htm.

*Primary Examiner* — John Pauls
(74) *Attorney, Agent, or Firm* — Mark R. Malek, Esq.; Daniel C. Pierron; Zies Widerman & Malek

(57) ABSTRACT

A medical claim fraud prevention system includes a first controller positioned at a medical facility and a second controller positioned at a patient information collection center and adapted to be in communication with a data center having historical location information relating to a patient locating device. The first controller may transmit a first signal to the second controller responsive to an occurrence of a predetermined event. The second controller may transmit an indication to the first controller in response to the first signal received from the first controller regarding the historical location of the patient locating device and whether the patient locating device was within a predetermined vicinity of the medical facility during a predetermined time period.

26 Claims, 29 Drawing Sheets

U.S. PATENT DOCUMENTS

| | | |
|---|---|---|
| 2002/0032584 A1 | 3/2002 | Doctor et al. |
| 2002/0049612 A1 | 4/2002 | Jaeger et al. |
| 2002/0087358 A1 | 7/2002 | Gilbert |
| 2002/0116224 A1 | 8/2002 | Hengerer et al. |
| 2002/0120471 A1 | 8/2002 | Drazen |
| 2002/0143579 A1 | 10/2002 | Docherty et al. |
| 2002/0143582 A1 | 10/2002 | Neuman et al. |
| 2003/0055679 A1 | 3/2003 | Soll et al. |
| 2003/0120512 A1 | 6/2003 | Dengler |
| 2003/0158755 A1 | 8/2003 | Neuman |
| 2003/0182194 A1 * | 9/2003 | Choey et al. .................. 705/16 |
| 2003/0212576 A1 | 11/2003 | Kim |
| 2003/0233250 A1 | 12/2003 | Joffe et al. |
| 2004/0015337 A1 | 1/2004 | Thomas et al. |
| 2004/0078220 A1 | 4/2004 | Jackson |
| 2004/0143454 A1 * | 7/2004 | Kimmel ........................... 705/2 |
| 2004/0153338 A1 | 8/2004 | Kim et al. |
| 2004/0260577 A1 | 12/2004 | Dahlin et al. |
| 2004/0260666 A1 | 12/2004 | Pestotnik et al. |
| 2004/0267572 A1 | 12/2004 | Emery et al. |
| 2006/0237531 A1 * | 10/2006 | Heffez et al. ................. 235/382 |
| 2007/0299776 A1 | 12/2007 | Frustaci |
| 2009/0204434 A1 | 8/2009 | Breazeale |

* cited by examiner

MEDICAL CLAIMS FRAUD PREVENTION SYSTEM INCLUDING HISTORICAL PATIENT LOCATING FEATURE AND ASSOCIATED METHODS

RELATED APPLICATIONS

This application is a continuation in part of U.S. patent application Ser. No. 12/614,841 titled Medical Decision System Including Question Mapping and Cross Referencing System and Associated Methods filed on Nov. 9, 2009, which is a continuation-in-part of U.S. patent application Ser. No. 11/928,690 filed on Oct. 30, 2007, now U.S. Pat. No. 8,260,633 and titled Medical Decision Auditing Method and System, which, in turn, was a divisional application of U.S. patent application Ser. No. 11/191,304, now U.S. Pat. No. 7,464,042 filed on Jul. 28, 2005, now U.S. Pat. No. 7,464,042 and titled Medical Professional Monitoring System and Associated Methods, the entire contents of each of which are incorporated herein by reference. The present application is also related to U.S. patent application Ser. No. 12/614,910 titled Medical Decision System Including Interactive Protocols and Associated Methods filed on Nov. 9, 2009, and U.S. patent application Ser. No. 12/614,937 titled Medical Decision System including Medical Observation Locking and Associated Methods filed on Nov. 9, 2009, the entire contents of each of which are incorporated herein by reference. The present application is also related to U.S. patent application Ser. No. 12/832,427 titled Medical Claims Fraud Prevention System Including Patient Call Initiating Feature And Associated Methods by the inventors of the present application, U.S. patent application Ser. No. 12/832,354 titled Medical Claims Fraud Prevention System And Associated Methods by the inventors of the present application, and U.S. patent application Ser. No. 12/832,458 titled Medical Claims Fraud System Including Patient Identification Interface Feature And Associated Methods by the inventors of the present application, each filed simultaneously herewith, the contents of each of which are incorporated herein by reference.

FIELD OF THE INVENTION

The present invention relates to the systems for use in the medical field and, more specifically, to the field of preventing fraud in the field of medical insurance claims, and related methods.

BACKGROUND OF THE INVENTION

There has long been an issue regarding reimbursements of medical costs made by insurance companies. Typically, a medical services or medical products provider will provide a particular service or product to a patient and bill an insurance company for some portion of the cost of that service or product. In some cases, the insurance company is responsible for the entire cost of the service or product, but in most cases, the patient is responsible for some portion of the cost for these services and products.

In their never ending pursuit to enhance their profitability, insurance companies force medical professionals and medical supply companies to accept decreased payments. These are sometimes referred to as "negotiated" rates. The negotiated rates can amount to a much lower amount than a medical professional or medical supply company had planned on charging for their services or products. As time goes on, the negotiated rates tend to have an adverse affect on profitability. One effect of the decreased profitability is that some medical professionals and medical supply companies are forced to go out of business. Another effect, unfortunately, can be that in order to make up for the lost profits, some medical professionals and medical supply companies engage in fraudulent behaviors. These fraudulent behaviors may, for example, include submitting requests for reimbursements for medical expenses to insurance companies for medical services that were not rendered to a patient or for medical products that were not supplied to a patient. Fraudulent acts such as this have, in the past, been considered victimless crimes, i.e., the only one getting hurt is the insurance company. Accordingly, not much attention has been paid to this issue until it has become apparent that the fraudulent behavior may be a source of rising healthcare costs.

Current systems that are used to monitor medical services that are provided to patients are outdated and can be costly. For example, some insurance companies transmit a notice to a patient after a medical service has been provided. The notice indicates that medical service that has been provided and the portion of the service that was covered by the insurance company. This type of system carries out fraud prevention by putting the patient on notice of the type of service that a medical professional may be seeking reimbursement for. If the service did not occur, then a patient receiving the notification will likely contact the insurance company to clear up the discrepancy.

Several systems exist to conduct reviews of healthcare. For example, U.S. Pat. No. 5,359,505 to Little et al. discloses a healthcare payment and review system. The system reviews and adjudicates healthcare payment requests made by a healthcare provider for procedures performed. The system reviews the payment request based on user-specified review criteria. Such criterion may reflect contractual arrangements between payers, providers and patients, current, locally acceptable medical practices and patient and provider payment request patterns. To perform the review, the expert system obtains relevant prior payment requests and defines a master list of payable payment requests given current medical procedures. The system goes on to analyze the current payment request according to the relevant historical payment requests and the master payable list by applying user-defined interpretive rules to this information. Payment decisions are developed and reported based on the analysis.

Many times, medical services can only be provided to a patient when the patient is located the same location as the medical professional. There exist systems that track the location of patients. For example, U.S. Published Patent Application No. 2009/0204434 by Breazeale Jr. discloses a healthcare tracking system that obtains location-time data automatically generated by a mobile electronic device associated with a healthcare provider, and that correlates the location-time data with a location of the healthcare patient. This system, however, is directed to assuring that patients are billed for procedures that have been performed. The location information of the patient is used to reflect a triggering event for billing purposes.

U.S. Published Patent Application No. 2007/0299776 by Frustaci et al. discloses a method for preventing medical fraud that uses a real time transmitted identification system to verify patient identification, location, time and medical service provider identification. The system verifies provision of services to an authorized service user by assigning a unique identifying number to each authorized service provider and by assigning a unique identifying number to each authorized service user. The system determines the likelihood that an insurance claim by a service provider is valid by defining the unique identifying feature of each of the authorized patients and for each of the authorized doctors. Accordingly, the system is directed to determining probabilities of whether or not a medical claim may be fraudulent. The Frustaci et al. '776 patent application discloses that the patient's physical location may be determined by an attached GPS system at the provided location. The system obtains the patient's and the provider's fingerprints, or other identifying feature, and transmits the identifying feature information to a service confirmation center in real time.

U.S. Pat. No. 7,421,399 to Kimmel discloses a method of discouraging healthcare fraud in conjunction with providing healthcare services to patients in which the patient provides a biometric signature. More specifically, the system uses biometric information unique to an individual combined with location information to create a persistent record indicating that a particular person was physically present at a particular place.

SUMMARY OF THE INVENTION

With the above in mind, the present invention advantageously provides a medical claims fraud prevention system that readily confirms that a patient was present at the time that a medical claim is being made. The present invention also advantageously speeds up the time associated with a medical professional receiving their medical reimbursement. The present invention further advantageously provides many different ways to locate a patient so as to provide redundancies and backups to ensure that an appropriate medical claim is not rejected.

These and other objects, features, and advantages according to the present invention are provided by a medical claim fraud prevention system comprising a first controller positioned at a medical facility and a second controller positioned at a patient information collection center. The second controller is adapted to be in communication with the first controller.

The medical claim fraud prevention system may also include a patient locating device adapted to be within a predetermined vicinity of a patient and adapted to be in communication with the second controller to provide location data relating to the location of the patient locating device. The first controller may send a first signal to the second controller responsive to an occurrence of a predetermined event. The second controller may transmit an indication to the first controller in response to the first signal received from the first controller of whether the patient locating device is within a predetermined vicinity of the medical facility based on the location data relating to the location of the patient locating device.

The patient may be assigned a patient information unit having predetermined patient information associated therewith. The predetermined event may be reading information from the patient information unit. The first controller may be a patient information unit reader adapted to read the predetermined patient information associated with the patient information unit.

A medical software system in communication with the first controller may be used by a medical professional at the medical facility. While using the medical software system, the medical professional may be prompted to enter information relating to the patient. In such a case, the predetermined event may be entry of the information relating to the patient using the medical software system. Alternately, a billing system may be used at the medical facility to bill for medical services provided to the patient. In such a case, the predetermined event may be use of the billing system with respect to the patient. Accordingly, the system of the present invention advantageously provides several different options to prompt locating the patient.

The patient locating device may be a GPS enabled electronic device. The patient locating device may also be a signal emitting device capable of being triangulated to determine the location data. The medical facility may be a doctor's office, a hospital, a pharmacy, a therapy center, a medical laboratory, a medical clinic, a rehabilitation facility, a dialysis unit, an out-patient center, an assisted living facility, an emergency room, or a nursing home.

The patient information collection center may be associated with processing health insurance claims. The signal transmitted from the first controller to the second controller may include information relating to a claim for reimbursement relating to medical services being provided to the patient at the medical facility. The second controller may transmit a signal to the first controller including an indication of whether or not the claim is a valid claim based on the indication of whether the patient locating device is within the predetermined vicinity of the medical facility. Accordingly, the present invention advantageously decreases the time required to provide approval for a proposed medical claim.

The system may also include a backup locating system that is activated to perform a predetermined action based on a predetermined backup event. The predetermined backup event that activates the backup location system may be an indication received from the second controller that the patient locating device is not within the predetermined vicinity of the medical facility. The patient locating device may be a mobile telephone. The predetermined action may be calling the mobile telephone and speaking with the patient to determine the location of the patient. The predetermined action may also be calling the medical facility and requiring the patient to verify their location using a predetermined patient identifier. Alternately, the predetermined action may be calling the medical facility, speaking with the patient, and requiring the patient to verify their location using a predetermined patient identifier.

A method aspect of the present invention is for preventing medical claim fraud. The method may include transmitting a first signal from a first controller positioned at the medical facility to a second controller positioned at the patient information collection center responsive to an occurrence of a predetermined event. The method may also include transmitting an indication from the second controller to the first controller in response to the first signal received from the first controller of whether the patient locating device is within the predetermined vicinity of the medical facility based on the location data relating to the location of the patient locating device.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The system according to the present invention is a computerized system that requires the performance of one or more steps to be performed on or in association with a computerized device, such as, but not limited to, a server, a computer (i.e., desktop computer, laptop computer, netbook or a machine having a processor), a dumb terminal that provides an interface with a computer or server, a personal digital assistant mobile communications device, such as an iPhone, Blackberry or other similar device which provides computer or quasi-computer functionality, a mobile reader, such as a Kindle, which provides reader functionality that may be enabled through either internal components or connecting to an external computer, server or global communications network (such as the Internet) to take direction from or engage in processes which are then delivered to the mobile reader. It should be readily apparent to those of skill in the art that other types of devices, individually or in conjunction with an overarching architecture associated with an internal or external system, may be utilized to provide the "computerized" environment necessary for the at least one process step to be carried out in a machine/system/digital environment. It should be noted that the method aspects of the present invention are preferably computer implemented methods and, more particularly, at least one step is preferably carried out using a computerized device. In short, a computerized system according to the present invention is meant to include any device having a processor and a memory.

Figure 1:
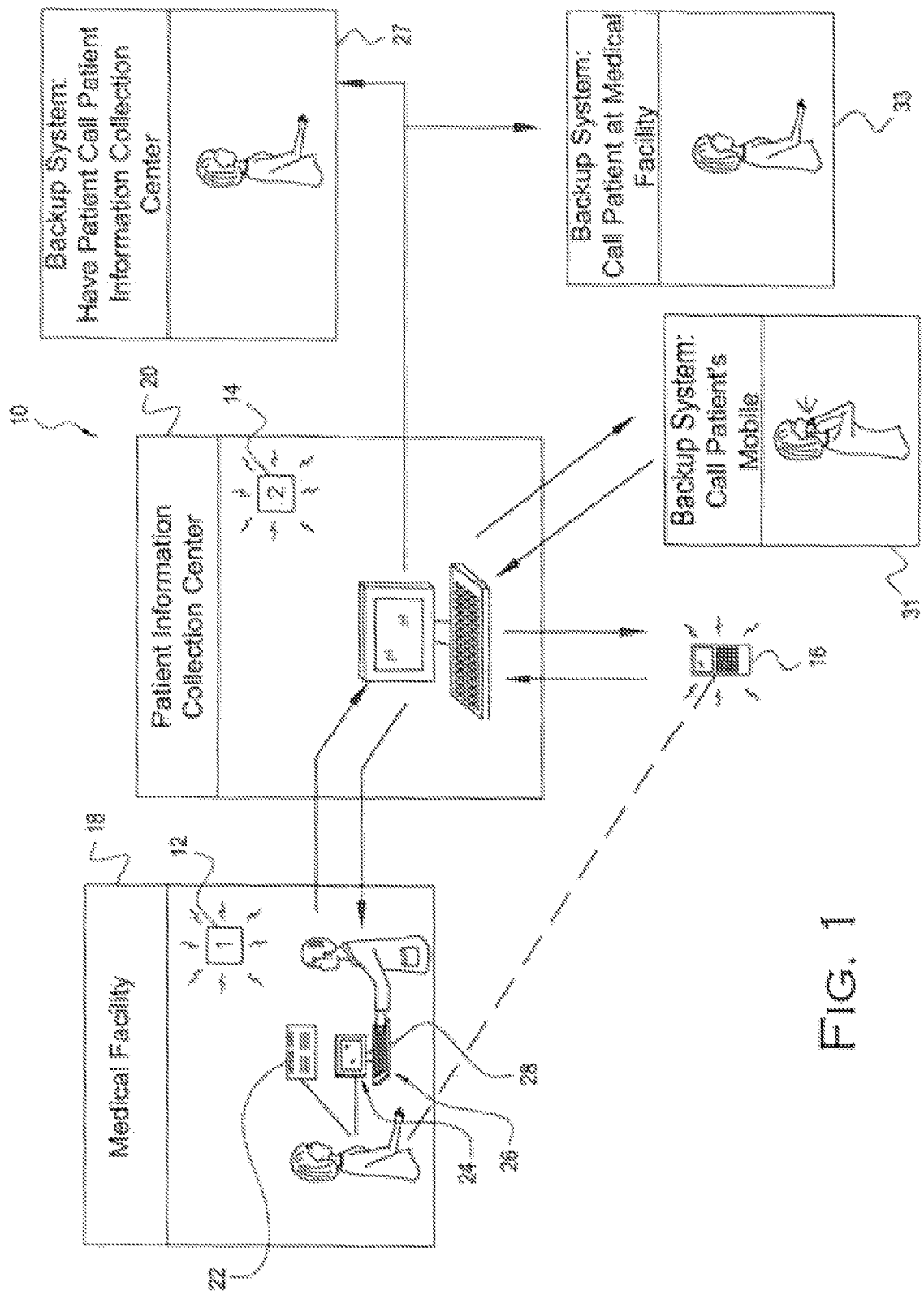
FIG. 1 is a schematic environmental view of a medical claim fraud prevention system according to the present invention.

Referring initially to FIG. 1, a medical claim fraud prevention system 10 according to the present invention is now described in greater detail. The medical claim fraud prevention system 10 illustrated in FIG. 1, according to an embodiment of the present invention, advantageously decreases medical claim fraud by verifying that a patient is located within a predetermined vicinity of a medical facility where medical services are being provided at the time that the medical services are being provided. This verification may be performed by ascertaining the location of a patient locating device 16 that is generally presumed to be on the person of a patient at the time of service. In this day and age, such a patient locating device 16 may, for example, be a patient's cell phone, i.e., a mobile telephone. As will be described in greater detail below, however, the patient locating device 18 may be any other type of device as well.

The predetermined vicinity within which the patient locating device 16 is expected to be within can be predetermined by any number of users of the system 10 according to an embodiment of the invention. For example, it may be desirous for the health insurance company to determine what vicinity is acceptable for the patient locating device 16 to be within. Alternately, it may be desirous for the patient to set the predetermined vicinity based on their personal habits. For example, a patient that generally always carries the device that may act as the patient locating device 16, i.e., the patient's cell phone, on their person, may desire that the predetermined vicinity be quite low, while the patient that generally leaves the device that may act as the patient locating device in their vehicles may wish for the predetermined vicinity to be somewhat greater. Accordingly, the system 10 according to the present invention advantageously allows for customization of the predetermined vicinity.

The system 10 according to an embodiment of the present invention also advantageously allows for the setting of the predetermined vicinity within which the patient locating device 16 must be in relation to the medical facility 18 where the medical services are being provided. This advantageously allows any of the above mentioned users to revise the predetermined vicinity as necessary.

The system 10 according to an embodiment of the present invention advantageously decreases medical claim fraud by determining the location of the patient locating device 16 at the time that medical services are provided. The time when medical services are being provided can be considered a window of time. For example, a determination that the patient locating device 16 is within the predetermined vicinity of the medical facility 18 at any time from when the patient first checks in with the receptionist (if applicable) to receive the medical services, up to and extending through the time the patient departs the medical facility 18 after having received the medical services may result in a positive indication, i.e., that the patient was within the predetermined vicinity of the medical facility when the medical services were being rendered, thereby indicating that the medical services were actually rendered to the patient and that medical claim fraud is not likely being committed. The system 10 according to an embodiment of the present invention even contemplates an extension of the time window to a predetermined time after the patient leaves the medical facility 18, but a short time nonetheless, i.e., within minutes. Those skilled in the art, however, will appreciate, after having had the benefit of reading this disclosure, that although it is preferable for the extended time window be a short one, i.e., minutes, it is possible and, in fact, contemplated by the present invention, that such a time window can be customized to the liking of the user. In such a case, the system 10 may be programmed to increase the range of the predetermined vicinity by a predetermined amount based on the time since the patent left the medical facility. For example, if it is determined that the patient left the medical facility two minutes prior to the system 10 being prompted to determine the location of the patient, then the predetermined vicinity may be increased to a range of 1.5 miles. Of course, those skilled in the art will appreciate that this is merely an example, and not meant to be limiting in any way.

The system 10 may include a first controller 12 positioned at a medical facility 18. As will be discussed in greater detail below, the first controller 12 may be provided in several different ways to achieve the objects, goals, features and advantages of the present invention. The first controller 12 may include a user interface to receive indications relating to the patient locating device 16. For example, it may be desirous to provide an indication that the patient locating device 16 may be within the predetermined vicinity of the medical facility 18 using a visual indication, an audible indication, or any other type of indication suitable for informing a user of the findings and determinations of the system 10. The indication may, for example, be an electronic mail, a pop-up message, or any number of indications suitable for informing the user of the determinations made by the system 10 with respect to the location of the patient locating device 16 and, by implication, location of the patient.

The system 10 may also include a second controller 14 positioned at a patient information collection center 20. The second controller 14 may be adapted to be in communication with the first controller 12. More specifically, the first and second controllers 12, 14 may be in communication with one another in any number of ways. After having had the benefit of reading this disclosure, those skilled in the art will appreciate that the first and second controllers 12, 14 may be positioned in communication with one another via a wireless connection, a modem, a radio link, a LAN, or any other type of connection suitable for allowing the first and second controllers 12, 14 to communicate with one another and to transmit data, in any form, and other information between one another. More particularly, the system 10 according to an embodiment of the present invention contemplates that data in the form of text, pictures, video or any other form may be transmitted between the first and second controllers 12, 14 to carry out the objects, features and advantages according to the present invention.

As briefly discussed above, the system 10 may include a patient locating device 16 adapted to be within a predetermined vicinity of a patient and adapted to be in communication with the second controller 14. Location data relating to the patient locating device 16 may be provided to the second controller 14. This information may be provided when requested by the second controller 14 or may be continuously provided by the patient locating device 16 via a continuous transmission therefrom. In a situation where the patient locating device 16 is continuously providing location data to the second controller 14, such data may be transmitted intermittently over a predetermined amount of time. Recognizing, however, that continuously transmitting data between the patient locating device 16 and the second controller 14 may cause congestion over communication lines of the system 10, i.e., network congestion, it is preferable for the patient locating device 16 to provide location data upon request.

As indicated above, the patient locating device 16 may, for example, be a patient's cell phone (also referred to herein as a mobile telephone, and to be understood to refer to any portable telephonic device). The patient locating device 16 may also be provided by any other type of signal emitting device that is adapted to be within a vicinity of the patient and, more particularly, adapted to be routinely carried by the patient. Other examples of the patient locating device 16 may include a key fob to be connected to a key ring, or even a small card including a transmitting device, e.g., a radio frequency transmitter, that can be readily carried within the wallet of a patient. A card version of the patient locating device 16 may advantageously be integrated with an insurance card carried by the patient so that the patient routinely has the patient locating device on their person when at a medical facility.

The patient locating device 16 may, for example, be a device that is enabled with a global positioning system, i.e., a GPS enable device. Those skilled in the art will appreciate, after having had the benefit of reading this disclosure, that most modern cell phones are GPS enabled, but the system 10 according to the present invention provides for use of other GPS enabled devices such as, for example, a GPS enabled personal digital assistant, a GPS enabled pager, a GPS enabled handheld device associated with providing medical care or any other GPS enabled device that may be carried within a general vicinity of a patient. General vicinity, for purposes of the system 10 according to the present invention, is meant to indicate a vicinity within which a patient is located, i.e., on the person of the patient, or within a close distance to the patient, i.e., in a patient's purse, bag, backpack, within the patient's vehicle, etc.

Similarly, the patient locating device 16 may be any signal emitting device that is capable of being triangulated to determine the location thereof. For example, non-GPS enabled cell phones, as well as some GPS enabled cell phones, emit a signal to various cellular towers. When within the vicinity of three cellular towers, the signal being emitted by such a cell phone may be readily triangulated to determine a location of the cell phone. Another example may, for example, be a pager, or even a walkie-talkie that may be carried for communication purposes by a patient. Those skilled in the art will appreciate, after having had the benefit of reading this disclosure, that the system 10 according to the present invention contemplates that any signal emitting device may be used as the patient locating device 16 while simultaneously accomplishing the goals, features and advantages according to the present invention.

The first controller 12 may send a first signal to the second controller 14 responsive to an occurrence of a predetermined event. In turn, the second controller 14 may transmit an indication to the first controller 12 in response to the first signal received from the first controller of whether the patent locating device 16 is within a predetermined vicinity of the medical facility 18. This indication may be based on the location data relating to the location of the patent locating device 16. Accordingly, the system 10 according to the present invention advantageously provides an indication of a location of the patient locating device 16 with respect to the medical facility 18 upon the occurrence of the predetermined event so that it may be determined whether or not the patient locating device is within the vicinity of the medical facility when, for example, medical services are rendered to the patient. Again, the present invention makes the assumption that the patient locating device 16 is a device that is within a general vicinity of the patient that is receiving the medical services or any other type of medical treatment, i.e., therapy, counseling, etc. at the medical facility 18. This embodiment of the system 10 according to the present invention assumes that the medical services are being rendered at the time that the predetermined event occurs which prompts a determination of the location of the patient locating device 16 with respect to the medical facility 18, or within a close proximity to the time that the predetermined event occurs.

In one embodiment of the system 10 according to the present invention, the patient may be assigned a patient information unit 22 having predetermined patient information associated therewith. The patient information unit 22 may, for example, be a patient insurance card. The patient insurance card may include a transmitting device embedded therein. For example, the patient insurance card may include a radio frequency transmitter embedded within a body portion thereof. The predetermined event that may trigger the action of determining the location of the patient locating device 16 may, for example, be reading information from the patient information unit 22. For example, when a patient presents the patient insurance card to a medical professional upon entering the medical facility 18 to receive medical services, or other types of medical treatment, the medical professional may read information from the patient insurance card using a device adapted to read patient information from the patient insurance card. Upon the occurrence of such event, the first controller 12 may send a first signal to the second controller 14 to determine a location of the patient locating device 16 with respect to the medical facility 18.

Accordingly, the first controller 12 may be provided by a patient information unit reader 24 that may be adapted to read the predetermined patient information associated with the patient information unit 22. By way of example, the patient information unit 22 may include a magnetic strip having patient information stored thereon. Further, the patient information unit reader 24 may include a magnetic strip reader adapted to read patient information from the magnetic strip on the patient information unit 22. Upon reading the patient information from the magnetic strip, the patient information may be loaded onto a software system used at the medical facility 18. Upon reading the medical information from the magnetic strip of the patient information unit 22, the first controller 12 may send the first signal to the second controller 14 to prompt retrieval of location data of the patient locating device 16. These skilled in the art will appreciate, after having had the benefit of reading this disclosure, that the first controller 12 may be integrally formed into the magnetic strip reader, or may be a standalone device adapted to be in communication with the magnetic card reader.

By way of an additional example, the patient information unit 22 may be a patient insurance card that includes a radio frequency transmitter embedded therein. The patient information unit reader 24 may include a radio frequency receiver adapted to receive a radio frequency signal transmitted from the patient insurance card. The radio frequency signal transmitted from the patient insurance card may, for example, include patient information relating to the patient, e.g., insurance information. Upon receiving the radio frequency signal from the patient information unit 22, the first controller 12 may send the first signal to the second controller 14 to prompt retrieval of location data of the patient locating device 16.

The patient information unit 22 may, for example, also be a card adapted to charge a health savings account of a patient. Health savings accounts are generally provided by insurance companies to their customers so that the customer may put money aside in a savings account. The funds that are put aside in the savings account are generally put aside prior to income tax being taken out, i.e., pre-tax. This advantageously encourages insurance customers to save a certain amount of money in order to pay for medical expenses that may arise, i.e., co-pays, deductibles, etc. A card, such as a debit card, for example, may be used to access these funds. Such funds may be accessed, for example, at the time that a co-pay is due from the patient. Co-pays are generally payable upon arrival at the medical facility prior to being seen by the medical professional. Accordingly, charging the debit card for the co-pay may be considered the predetermined event that prompts the first signal to be transmitted from the first controller 12 to the second controller 14 to determine the location of the patient locating device 16 with respect to the medical facility 18.

The system 10 according to an embodiment of the present invention contemplates that a medical software system 26 may be positioned in communication with the first controller 12. The medical professional may be prompted to enter information relating to the patient using the medical software system 26. Accordingly, the predetermined event that prompts a determination of the location of the patient locating device 16 may be entry of information relating to the patient using the medical software system 26.

This configuration of the system 10 according to the present invention is advantageous when a medical facility is not equipped with a patient information unit reader 24 that may read information from a patient information unit 22. In this configuration, the medical professional may manually enter information relating to the patient into the medical software system 26. Upon entering information relating to the patient into the medical software system 26, the first controller 12 may send the first signal to the second controller 14 to prompt retrieval of location data relating to the patient locating device 16. After having had the benefit of reading this disclosure, those having skill in the art will appreciate that any use of a medical software system 26 may be the predetermined event that prompts retrieval of location data of the patient locating device 16.

Another predetermined event that may prompt retrieval of location data relating to the patient locating device 16 may be use of a billing system at the medical facility 18 for medical services provided to the patient. Accordingly, upon entering information, or any use of the billing system at the medical facility 18 with respect to the patient, the first controller 12 may send the first signal to the second controller 14 to retrieve location data of the patient locating device 16.

The system 10 according to the present invention contemplates that the medical facility 18 may be a doctor's office, a hospital, a pharmacy, a therapy center, a medical laboratory, a medical clinic, a rehabilitation facility, a dialysis unit, an out-patient center, an assisted-living care facility, an emergency room, or a nursing home. Those skilled in the art will appreciate, however, that the system 10 according to the present invention may be used at any medical facility, and that the list provided above is exemplary in nature, and not meant to be limiting. The patient information collection center 20 is preferably associated with processing health insurance claims. Those skilled in the art will appreciate, however, that the patient information collection center may be any location outside the medical facility 18 where patient information may be gathered. A center associated with processing health insurance claims is preferable as that is likely the area where a medical fraud may be conducted, i.e., between the medical facility 18 and a patient information collection center 20 associated with processing health insurance claims, or some other sort of tampering with an insurance claim, Medicare/Medicaid claim, etc.

The signal transmitted from the first controller 12 to the second controller 14 may include information relating to a claim for reimbursement of medical services being provided to the patient at the medical facility 18. More specifically, the signal transmitted from the first controller 12 to the second controller 14 may include a request for reimbursement of the medical treatment, or other medical services being provided to the patient at the medical facility 18 so that more immediate or more rapid payment of the medical services being provided to the patient are provided to the medical professional. This advantageously enhances efficiency of the provision of medical services and payments for same, as well as enhances collection efforts of medical professionals when dealing with health insurance companies, for example. The second controller 14 may transmit a signal to the first controller including an indication of whether or not the claim is a valid claim based on the indication of whether or not the patient locating device 16 is within the predetermined vicinity of the medical facility 18.

As also illustrated in FIG. 1, the system 10 according to the present invention also includes a backup locating system that may be activated to perform a predetermined action based on the occurrence of a predetermined backup event. The predetermined backup event that activates the backup locating system may, for example, be an indication received from the second controller 14 that the patient locating device 16 is not within the predetermined vicinity of the medical facility 18. Several other type events, may be considered as the predetermined backup event that triggers activation of the backup locating, system such as, for example; a malfunction in sending the first signal from the first controller 12 to the second controller 14, or a malfunction in sending the indication of whether or not the patient locating device 16 is within the predetermined vicinity of the medical facility 18.

As illustrated in schematic box 31 in FIG. 1, the predetermined action may, for example, be calling the cell phone, i.e., mobile telephone, of the patient and speaking with the patient to determine the location of the patient. As illustrated in schematic box 33 in FIG. 1, the predetermined action may, alternately, be calling the medical facility 18 and requiring the patient to verify their location using a predetermined patient identifier. Such calls may, for example, be automated calls that require entry of a predetermined code using the keypad of the telephone. The predetermined action may further be providing a notification to the medical facility 18 including a request that the patient contact the patient information collection center 20 to verify the patient's location as illustrated, for example, in schematic box 27. In other words, the medical facility 18 may be called, or otherwise contacted, and provided with a request to ask the patient to call the patient information collection center 20. This can allow the patient to use any telephone in order to contact the patient information collection center 20 to thereby verify that the patient is within the predetermined vicinity of the medical facility 18. The present invention contemplates that the medical facility 18 may be contacted in any number of ways to provide the request for the patient to contact the patient information collection center 20. For example, an electronic message may be transmitted to the medical facility 18 via electronic mail or via another type of electronic communication medium, as understood by those skilled in the art. Similarly, it is contemplated that the patient may contact the patient information collection center 20 in any manner, i.e., calling the patient information collection center or even transmitting a response electronic message to the patient information collection center, as understood by those skilled in the art.

The predetermined action may also be calling the medical facility 18 and speaking with the patient (also illustrated in schematic box 33 in FIG. 1). This predetermined action may require the patient to verify their location using a predetermined patient identifier that may be spoken by the patient. For example, a customer service representative may initiate a phone call to the medical facility 18 upon activation of the backup locating system, and speak to the patient and require the patient to provide a predetermined patient identifier to verbally verify the patients location at the medical facility. The predetermined patient identifier may, for example, be the patient's date of birth, a pin code selected by the patient, a pin code that is preselected for the patient, or some other identifying information relating to the patient to verify that the patient is located within the vicinity of the medical facility 18 at the time that medical services are being provided to the patient, and that would routinely only be known by the patient.

Those skilled in the art will appreciate, after having had the benefit of reading this disclosure, that the system 10 according to the present invention may advantageously use biometric sensors to satisfy a number of features. For example, a biometric sensor may be positioned at the medical facility 18 to read a biometric feature of a patient, i.e., a thumb print, a finger print, an eye scan, etc., of a patient. This can advantageously be used to verify the identity of the patient that presents at the medical facility 18. This can also be used to prompt a determination of the location of the patient locating device 16 with respect to the medical facility. For example, the biometric sensor may be positioned in communication with the first controller 12, thereby prompting the first controller to send the first signal to determine the location of the patient locating device with respect to the medical facility at the time that the biometric sensor senses a biometric feature of the patient. Alternately, the biometric sensor may be integrally formed into the first controller 12. Either arrangement provides the advantage of automatically determining a location of the patient locating device 16 upon determining the identity of the patient at the medical facility.

Figure 2:
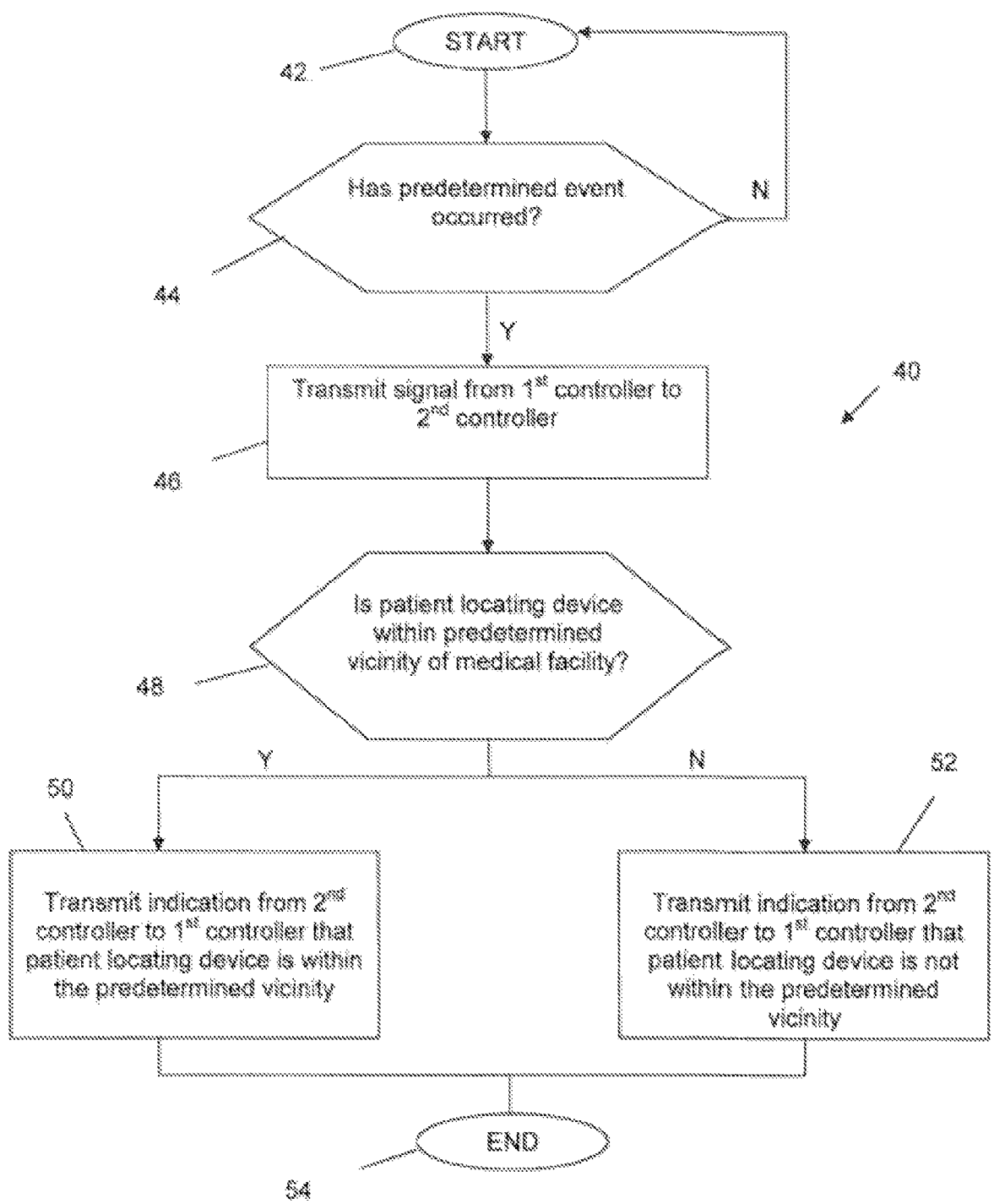
FIGS. 2-9 are flowcharts illustrating methods of preventing a medical claim fraud according to the present invention.

Referring now additionally to the flowchart 40 illustrated in FIG. 2, a method aspect of the present invention is now described in greater detail. The method according to the present invention, and as illustrated in the flowchart 40 of FIG. 2, is directed to preventing medical claim fraud by determining the location of a patient locating device and by ensuring that the patient locating device is within a predetermined vicinity of the medical facility where medical services are being provided. From the start (Block 42), it is determined at Block 44 whether the predetermined event has occurred. If it is determined at Block 44 that the predetermined event has not occurred, then the system reverts back to the start Block 42 to await occurrence of the predetermined event. If it is determined at Block 44, however, that the predetermined event has occurred, a first signal is transmitted from the first controller to the second controller at Block 46

At Block 48, it is determined whether or not the patient locating device is within the predetermined vicinity of the medical facility at the time that the medical services are being provided to the patient. If it is determined at Block 48 that the patient locating device is within the predetermined vicinity of the medical facility at the time that medical services are being provided to the patient, then an indication is transmitted from the second controller to the first controller that the patient locating device is within the predetermined vicinity at Block 50. If, however, it is determined at Block 48 that the patient locating device is not within the predetermined vicinity of the medical facility at the time that medical services are being provided to the patient, then an indication is transmitted from the second controller to the first controller that the patient locating device is not within the predetermined vicinity at Block 52. The method is ended at Block 54. Accordingly, the method illustrated in the flowchart 40 in FIG. 2 provides an indication of whether or not the patient is within a predetermined vicinity of a medical facility when a predetermined event occurred (wherein the predetermined event is an indication that medical services are being provided to the patient) to advantageously minimize medical claim fraud that may occur by identifying those instances when a medical claim is being made when a patient is not present at the time that medical services are allegedly being provided.

Figure 3:
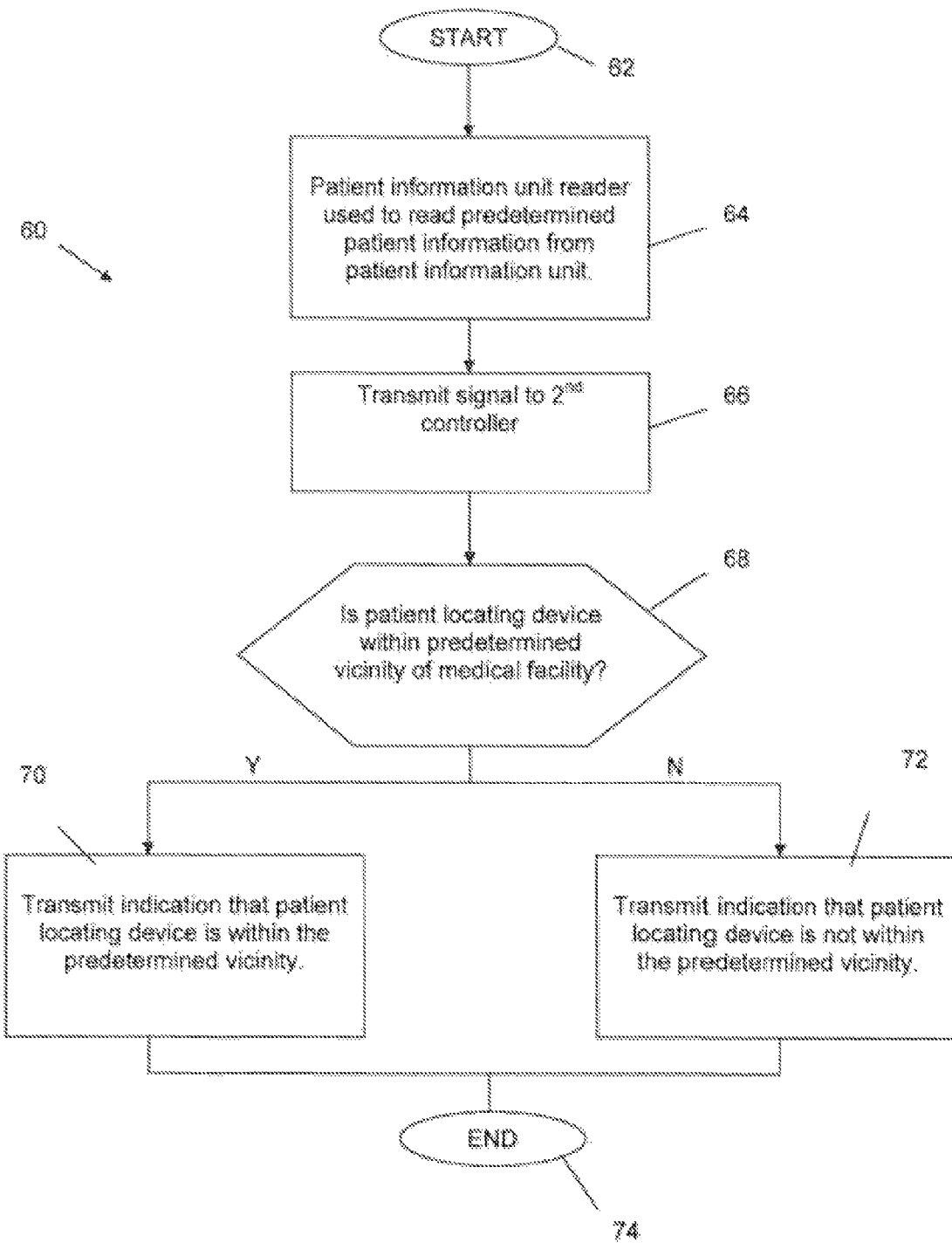

Referring now additionally to the flowchart 60 illustrated in FIG. 3, another method aspect of the present invention is now described in greater detail. More particularly, the method aspect of the invention depicted in the flowchart 60 of FIG. 3 illustrates one of the predetermined events that may prompt determining the location of the patient locating device with respect to the medical facility. From the start (Block 62), a patient information unit reader is used to read predetermined patient information from a patient information unit at Block 64. Upon reading the predetermined patient information from the patient information unit, a first signal is transmitted from the first controller to the second controller at Block 66. More specifically, and as discussed in greater detail above, the patient information unit reader may act as the first controller 12, and the first signal may be transmitted from the patient information unit reader to the second controller upon using the patient information unit reader to read predetermined information from the patient information unit.

At Block 68, it is determined if the patient locating device is within the predetermined vicinity of the medical facility at the time that the patient information unit reader is used to read predetermined patient information from the patient information unit (wherein reading predetermined patient information from the patient information unit using a patient information unit reader is an indication that the medical services are being provided to the patient). If it is determined at Block 68 that the patient locating device is within the predetermined vicinity of the medical facility at the time the medical services are being provided to the patient, then an indication is transmitted back to the first controller that the patient locating device is within the predetermined vicinity at Block 70. If, however, it is determined at Block 68 that the patient locating device is not within the predetermined vicinity of the medical facility at the time the patient information unit reader is used to read the predetermined patient information from the patient information unit, then an indication is transmitted that the patient locating device is not within the predetermined vicinity of the medical facility at Block 72. Accordingly, the predetermined event that prompts a determination of the location of the patient locating device with respect to the medical facility in the method aspect of the invention illustrated in the flowchart 60 of FIG. 3 is reading predetermined patient information from the patient information unit using the patient information unit reader. The method is ended at Block 74.

Figure 4:
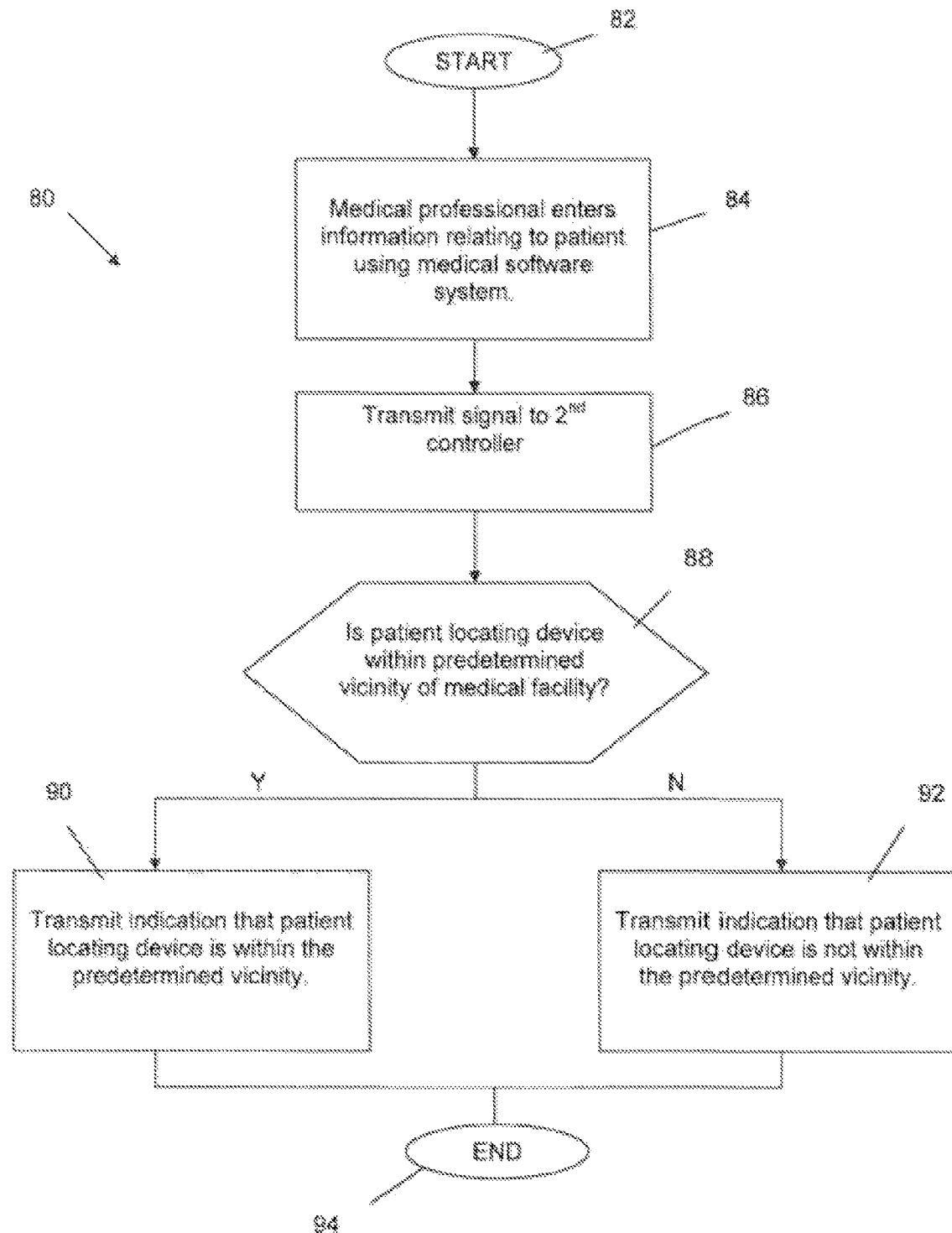

Referring now additionally to the flowchart 80 illustrated in FIG. 4, still another method aspect according to an embodiment of the present invention is now described in greater detail. In the method of the invention illustrated in the flowchart 80 of FIG. 4, the predetermined event that prompts a determination of the location of the patient locating device with respect to the medical facility is use of a medical software system with respect to a patient. From the start (Block 82), the medical professional may enter information relating to a patient using a medical software system at Block 84. At Block 86, a first signal may be transmitted from the first controller to the second controller.

At Block 88, it is determined if the patient locating device is within the predetermined vicinity of the medical facility at the time that the medical professional enters information relating to the patient using the medical software system (wherein use of the medical software system with respect to the patient is an indication that the medical services are being provided to the patient). If it is determined at Block 88 that the patient locating device is within the predetermined vicinity of the medical facility at the time the medical professional uses the medical software to enter information relating to the patient then an indication is transmitted that the patient locating device is within the predetermined vicinity of the medical facility at Block 90. If, however, it is determined at Block 88 that the patient locating device is not within the predetermined vicinity of the medical facility at the time the medical software system is being used by the medical professional to enter information relating to the patient, then an indication is transmitted that the patient locating device is not within the predetermined vicinity of the medical facility at Block 92. Accordingly, in this method aspect of the invention, the predetermined event that prompts the first signal to be transmitted from the first controller to the second controller to determine the location of the patient locating device with respect to the medical facility is use of the medical software system with respect to the patient. The method is ended at Block 94.

Figure 5:
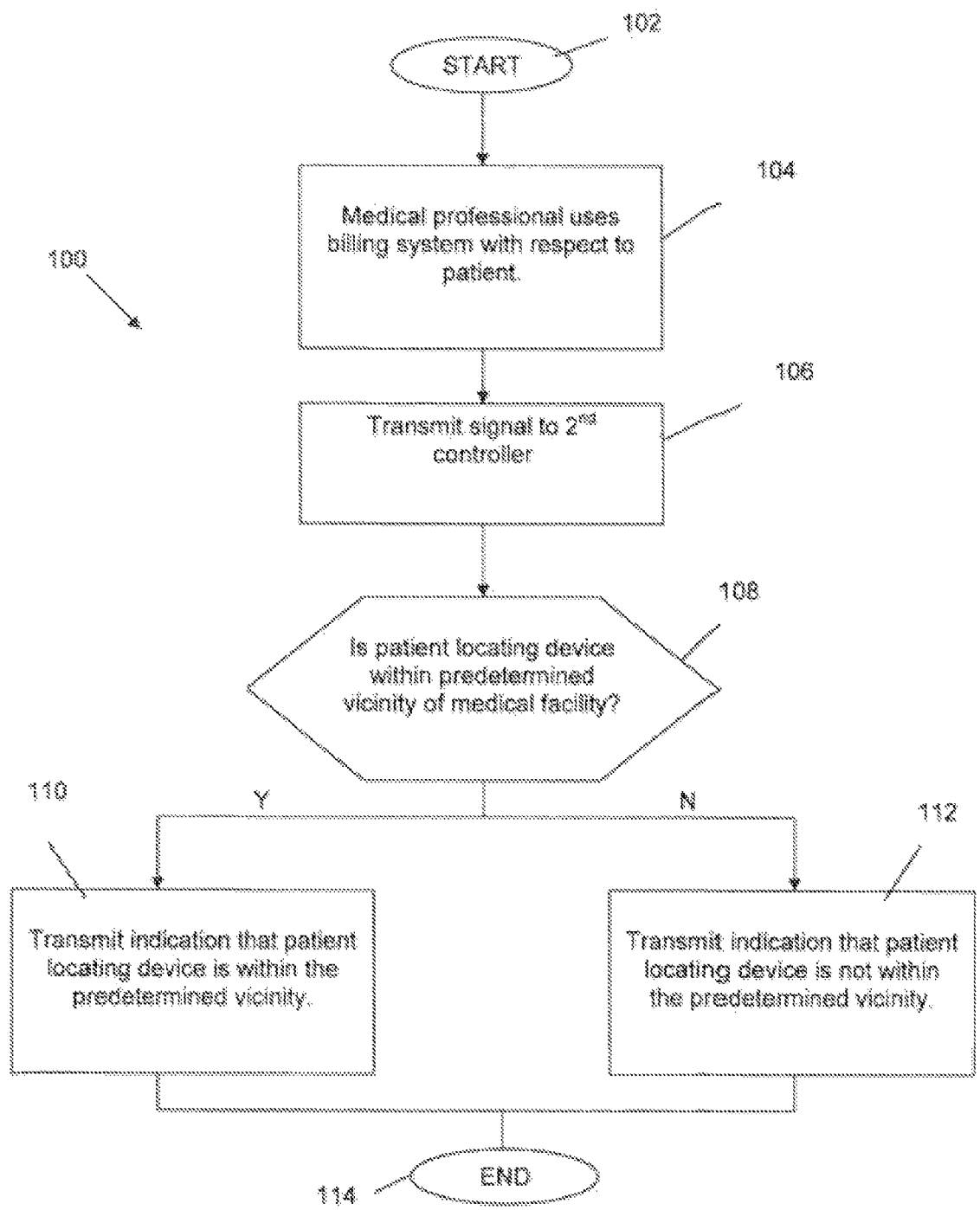

Referring now additionally to the flowchart 100 illustrated in FIG. 5, yet another method aspect according to an embodiment of the present invention is now described in greater detail. In the method aspect of the present invention illustrated in the flowchart 100 of FIG. 5, the predetermined event that prompts a determination of the location of the patient locating device with respect to the medical facility is use of a billing system with respect to the patient that is receiving medical services. From the start (Block 102), the medical professional may use a billing system with respect to the patient at Block 104. At Block 106, the first controller may transmit a first signal to the second controller to prompt determination of a location of the patient locating device.

At Block 108, it is determined whether the patient locating device is within the predetermined vicinity of the medical facility at the time that the medical professional uses the billing system with respect to the patient (wherein use of the billing system with respect to the patient is an indication that the medical services are being provided to the patient). If it is determined at Block 108 that the patient locating device is within the predetermined vicinity of the medical facility at the time the medical professional uses the billing system with respect to the patient, then an indication is transmitted at Block 110 that the patient locating device is within the predetermined vicinity of the medical facility. If, however, it is determined at Block 108 that the patient locating device is not within the predetermined vicinity of the medical facility at the time the medical services are being provided to the patient, then an indication is transmitted at Block 112 that the patient locating device is not within the predetermined vicinity. Accordingly, this method aspect of the present invention utilizes use of the billing system by the medical professional with respect to the patient to prompt transmittal of the first signal from the first controller and a determination of location of the patient locating device. The method is ended at Block 114.

Figure 6:
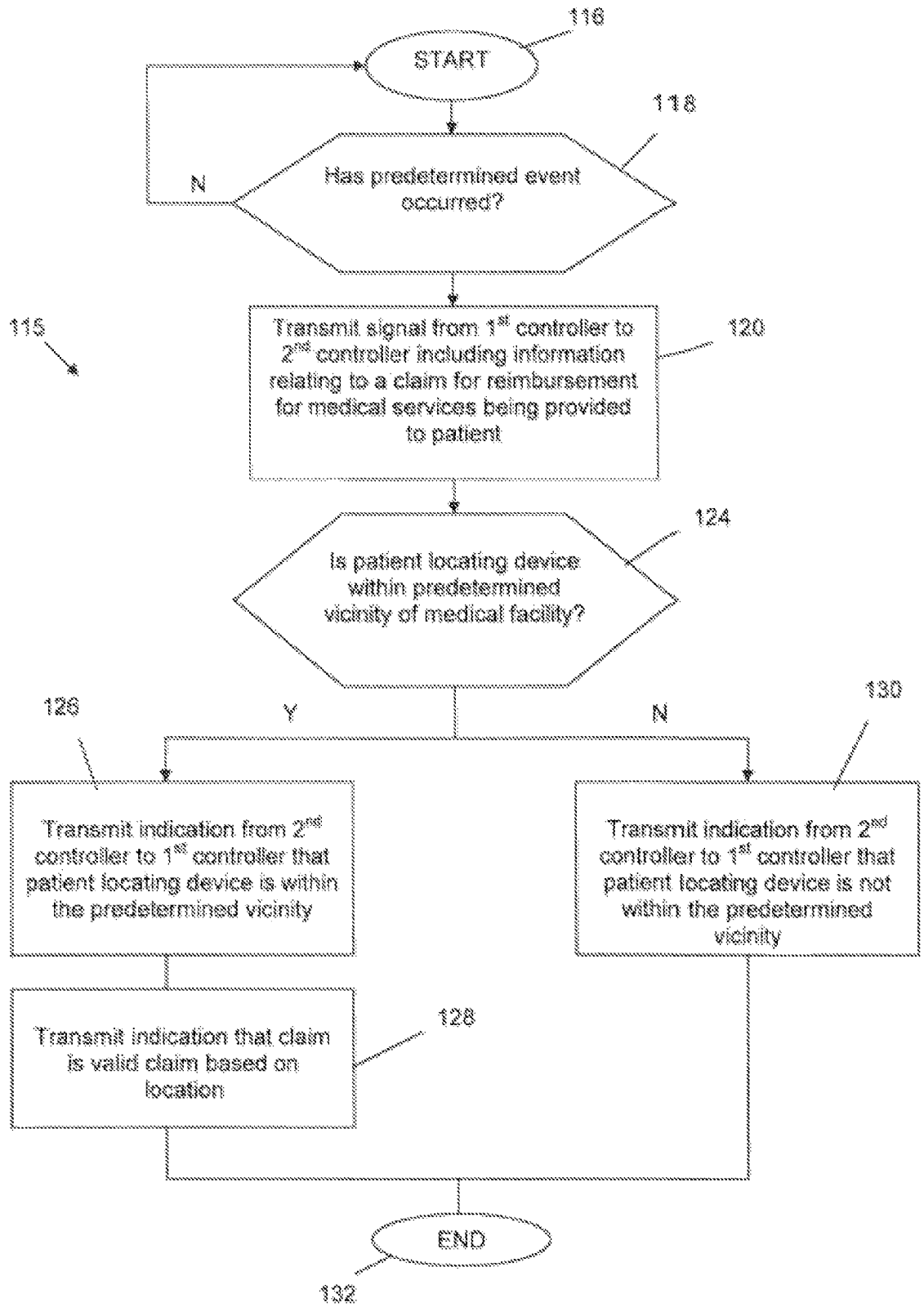

Referring now additionally to the flowchart 115 illustrated at FIG. 6, yet another method aspect according to an embodiment of the present invention is now described in greater detail. More specifically, the method illustrated in FIG. 6 is directed to a method of preventing medical claim fraud by locating a patient locating device to ensure that the patient locating device is within a predetermined vicinity of the medical facility at the time the medical services are being provided to the patient that includes transmitting a claim for reimbursement to a medical insurance company at the same time that the location of the patient locating device is determined. From the start (Block 116), it is determined at Block 118 whether or not the predetermined event has occurred. If it is determined at Block 118 that the predetermined event has not occurred, then the method reverts back to the start at Block 116. If, however, it is determined that the predetermined event has occurred at Block 118, then a first signal is transmitted from the first controller to the second controller at Block 120. The signal may include information relating to a claim for reimbursement for medical services being provided to the patient, along with a request to determine the location of the patient locating device.

At Block 124, it is determined if the patient locating device is within the predetermined vicinity of the medical facility at the time that the predetermined event has occurred (wherein occurrence of the predetermined event is an indication that the medical services are being provided to the patient). If it is determined at Block 124 that the patient locating device is within the predetermined vicinity of the medical facility at the time the medical services are being provided to the patient, then an indication is transmitted from the second controller to the first controller that the patient locating device is within the predetermined vicinity at Block 126.

Thereafter, at Block 128, an indication is transmitted that the claim is valid based on the location of the patient locating device with respect to the medical facility. If, however, the patient locating device is not within the predetermined vicinity of the medical facility at the time the medical services are being provided to the patient, then an indication is transmitted from the second controller to the first controller that the patient locating device is not within the predetermined vicinity at Block 130. By implication, of course, if the patient locating device is not within the predetermined vicinity of the medical facility at the time that the predetermined event occurs, the claim for those medical services are necessarily invalid. Thereafter, the method is ended at Block 132.

Figure 7:
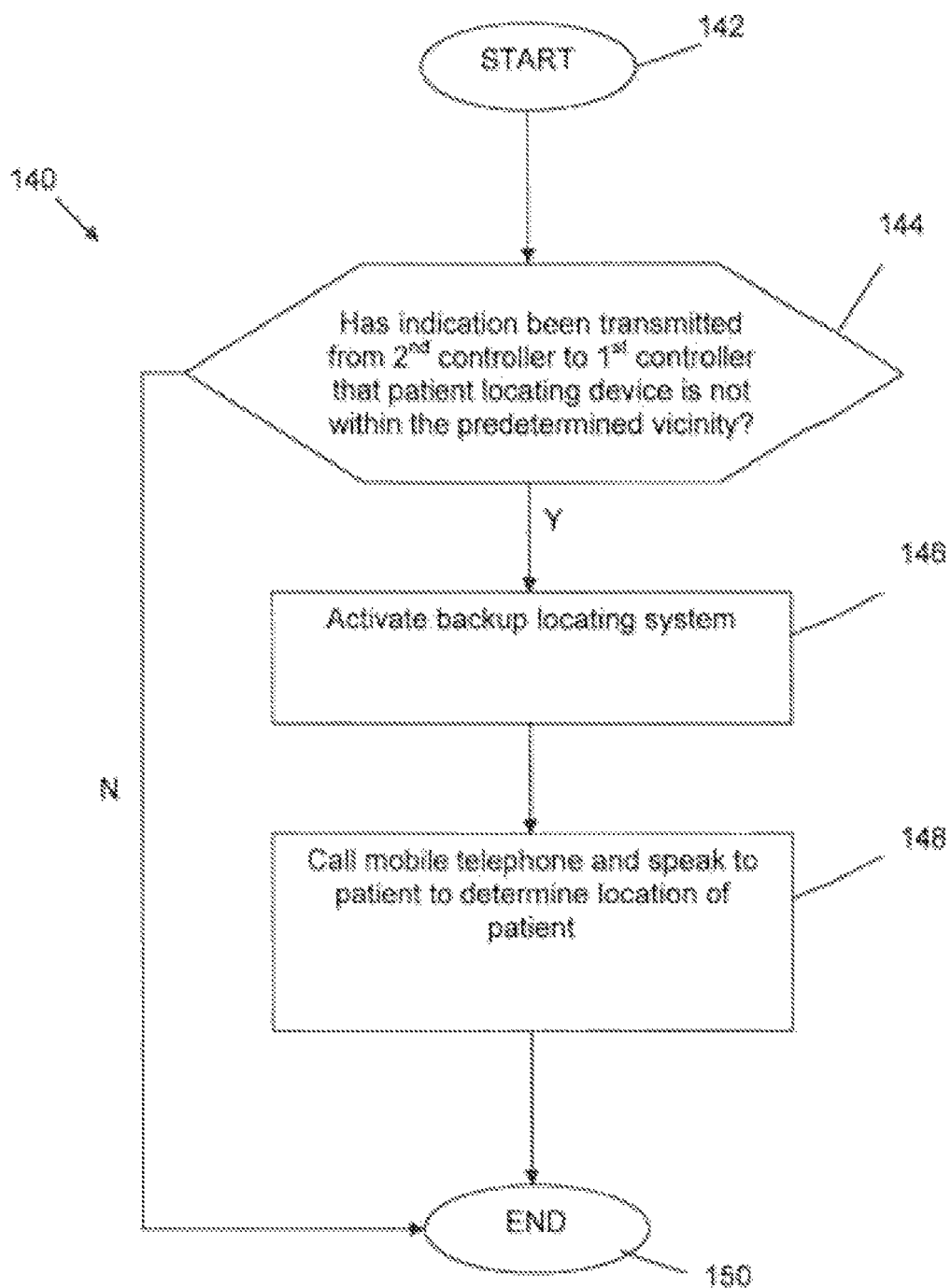

Referring now additionally to the flowchart 140 illustrated in FIG. 7, still another method aspect of the present invention is now described in greater detail. The method aspect of the present indention illustrated in the flowchart 140 of FIG. 7 illustrates use of a backup locating system according to the present invention. More specifically, from the start (Block 142), it is determined whether or not an indication has been transmitted from the second controller to the first controller that the patient locating device is not within the predetermined vicinity of the medical facility at the time the medical services are being provided to the patient at Block 144. If it is determined that an indication has not been transmitted from the second controller to the first controller that the patient locating device is not within the predetermined vicinity of the medical facility at the time the medical services are being provided to the patient at Block 144, then the method is ended at Block 150.

If, however, it is determined at Block 144 that an indication has been transmitted from the second controller to the first controller that the patient locating device is not within the predetermined vicinity of the medical facility at the time the medical services are being provided to the patient, then the backup locating system is activated at Block 146. At Block 148, a call is prompted to the patient's mobile telephone. Upon calling the patient's mobile telephone at Block 148, the patient may be prompted to verify their location. This may be performed by speaking to the patient, or in other ways that have been described above. Thereafter, the method is ended at Block 150.

Figure 8:
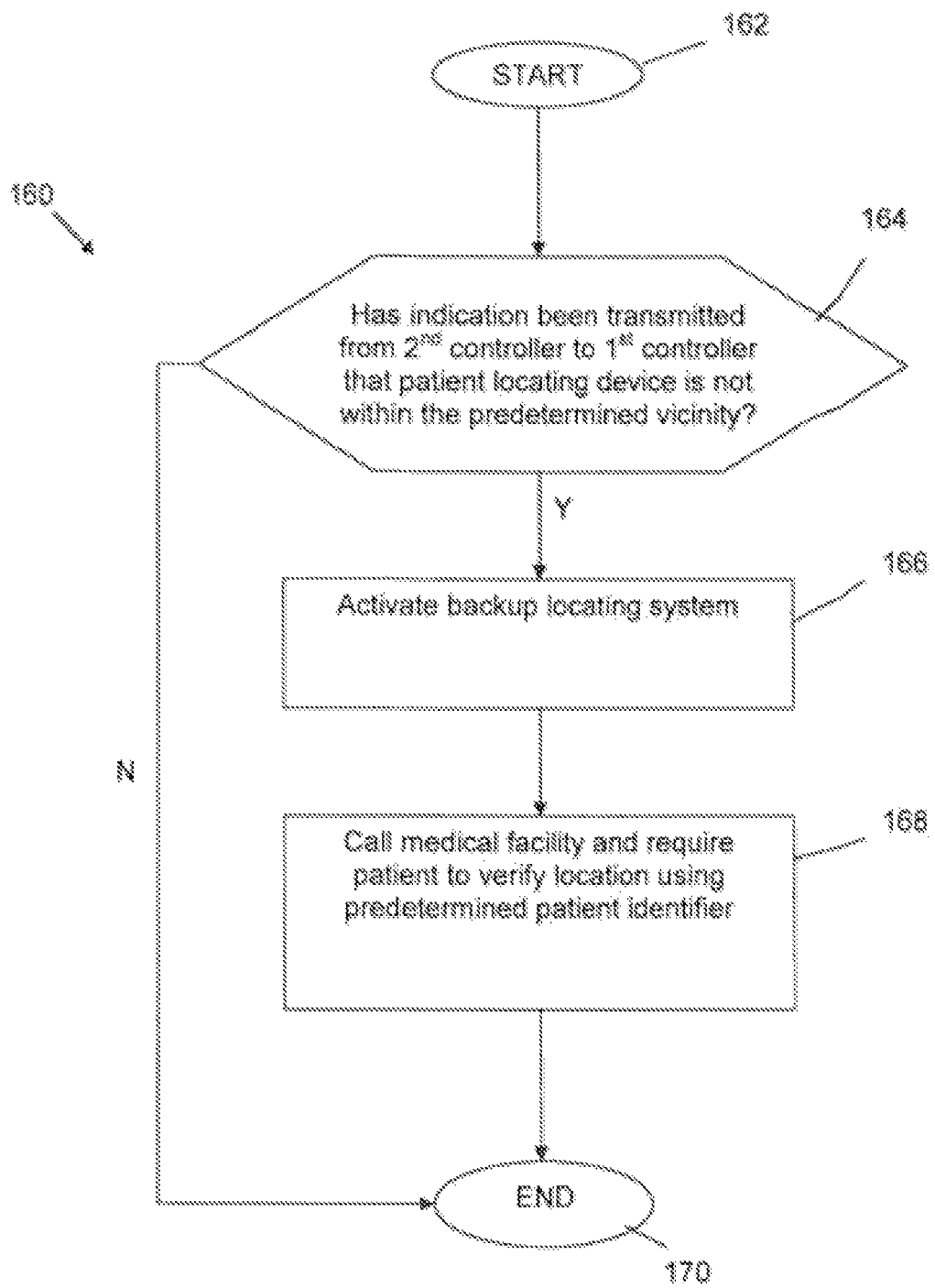

Referring now additionally to the flowchart 160 illustrated in FIG. 3, yet another method aspect of the present invention is now described in greater detail. The method aspect of the invention illustrated in the flowchart 160 of FIG. 8 provides greater detail as to use of the backup locating system. More specifically, from the start (Block 162), it is determined at Block 164 whether or not an indication has been transmitted from the second controller to the first controller that the patient locating device is not within the predetermined vicinity of the medical facility at the time the medical services are being provided to the patient. If it is determined at Block 164 that the patient locating device is not within the predetermined vicinity of the medical facility at the time the medical services are being provided to the patient, then the method is ended at Block 170. If, however, it is determined at Block 164 that the patient locating device is within the predetermined vicinity of the medical facility at the time the medical services are being provided to the patient, then the backup locating system is activated at Block 166. At Block 168, the medical facility is called and the patient is required to verify their location using a predetermined patient identifier, as described in greater detail above. Thereafter, the method is ended at Block 170.

Figure 9:
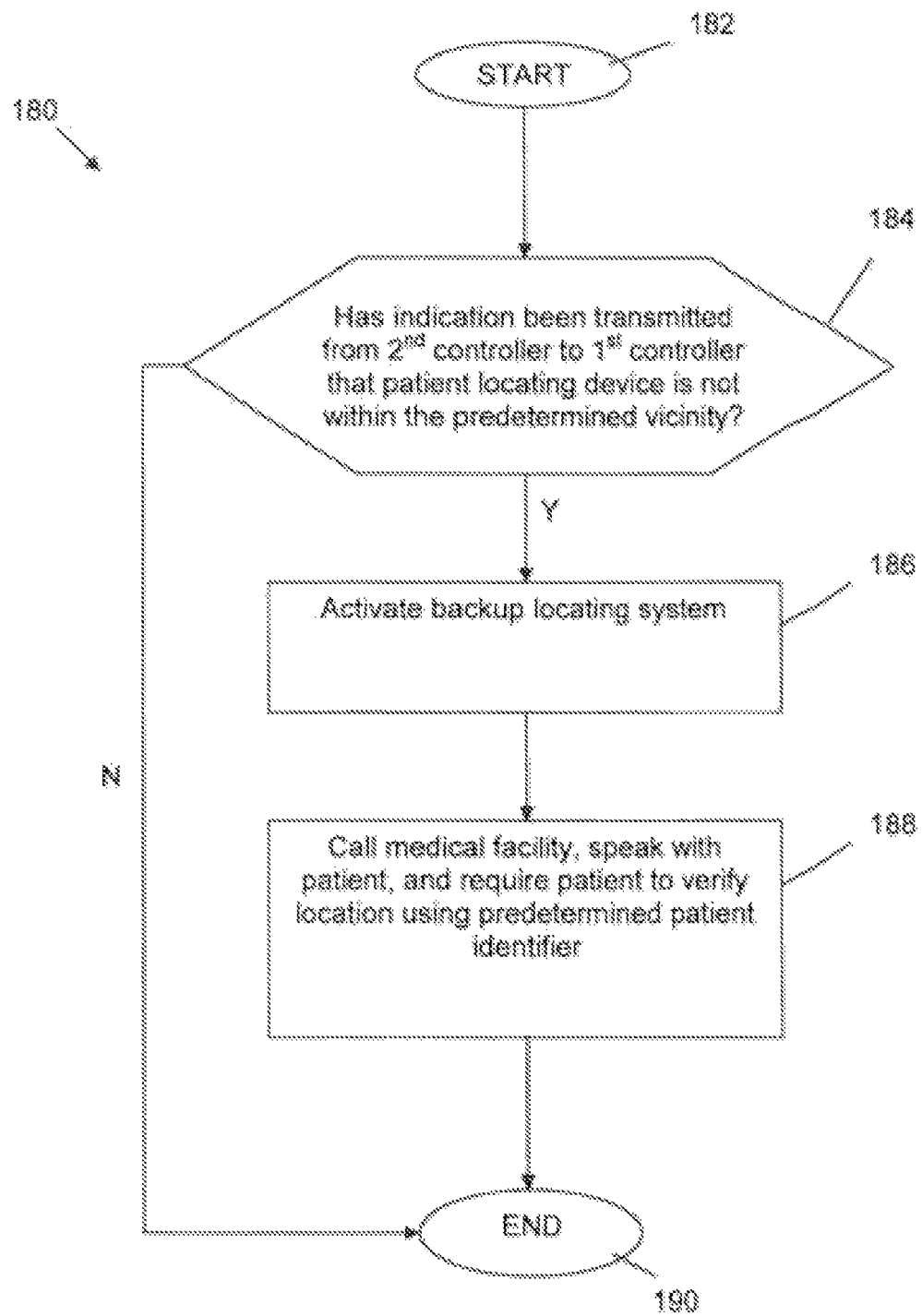

Referring now additionally to the flowchart 180 illustrated in FIG. 9, another aspect of an embodiment according to the present invention is now described in greater detail. The method illustrated in the flowchart 180 of FIG. 9 is directed to additional use of the backup locating system according to the present invention. More specifically, from the start (Block 182), it is determined whether or not an indication has been transmitted from the second controller to the first controller that the patient locating device is not within the predetermined vicinity of the medical facility at Block 184 at the time the medical services are being provided to the patient. If it is determined that the indication has not been transmitted at Block 184, then the method is ended at Block 190. If, however, it is determined at Block 184 that the indication has been transmitted, then the backup locating system is activated at Block 186. At Block 188, the medical facility is called, and the patient is spoken to and required to verify their location using a predetermined patient identifier. The method is ended at Block 190.

Figure 10:
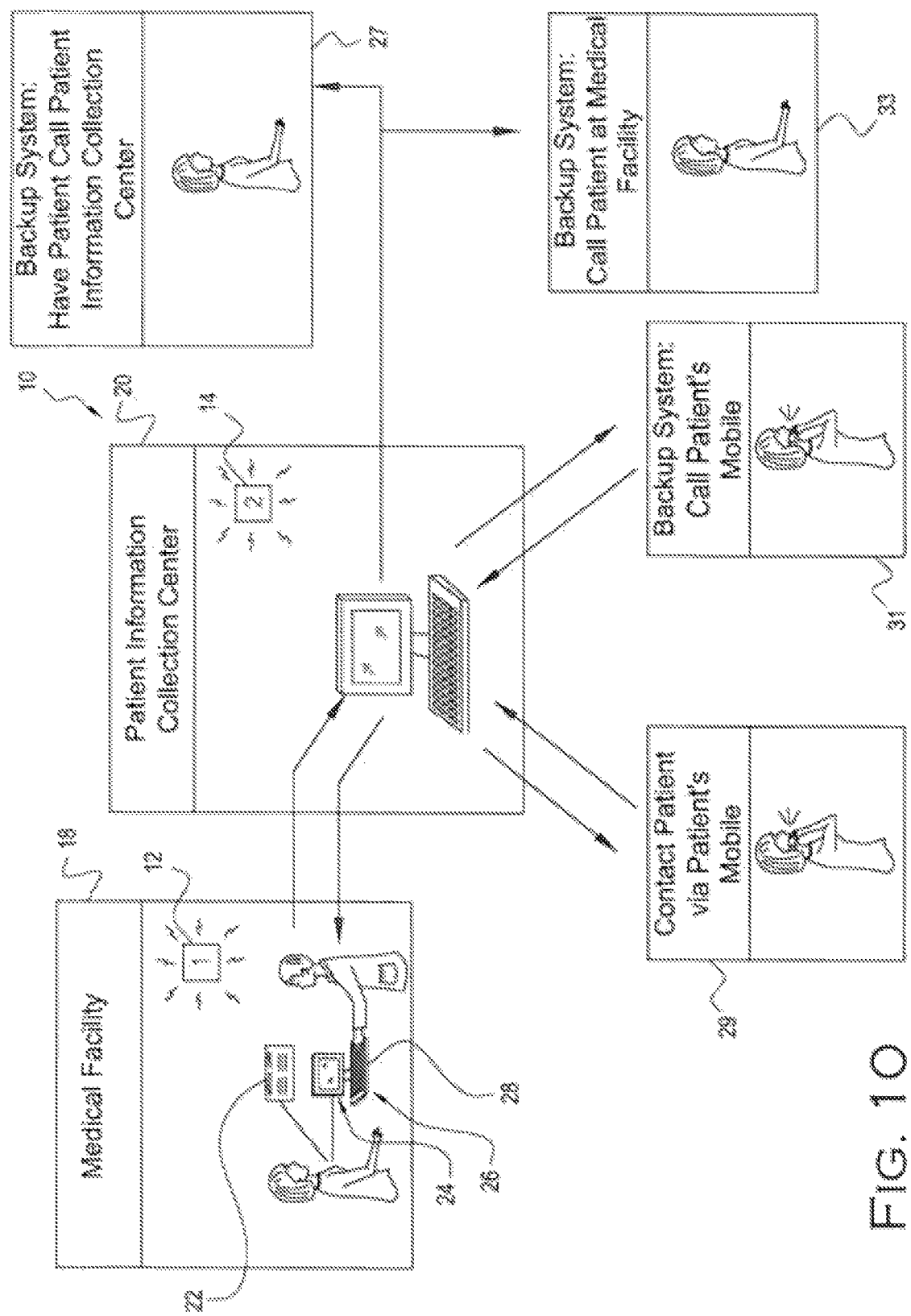
FIG. 10 is a schematic environmental view of an alternate embodiment of the medical claim fraud prevention system according to the present invention.

Referring now to FIG. 10, an alternate embodiment of the medical claim fraud prevention system 10 according to the present invention is now described in greater detail. In this embodiment of the medical claim fraud prevention system 10, the location of the patient may be confirmed while the patient is at the medical facility 18 when a predetermined event occurs by initiating a telephone call. As discussed in greater detail above, the predetermined event indicates the time at which the medical services are being provided to the patient. More specifically, the first controller 12 may be positioned at the medical facility 18, and the second controller 14 may be positioned at the patient information collection center 20 and adapted to be in communication with the first controller. The first controller 12 may send a first signal to the second controller 14 responsive to an occurrence of a predetermined event.

Thereafter, the second controller 14 may initiate a form of communication to a patient's mobile phone in response to the first signal received from the first controller 12, as illustrated, for example, in schematic box 29 in FIG. 10. Those skilled in the art will appreciate, after having had the benefit of reading this disclosure, that contacting the patient's mobile phone to verify the patient's location may be performed in any number of ways. For example, the patient's mobile phone may be called to contact the patient. This call may be made by a person, or may be an automated call. Further, a text message may be sent to the patient's mobile phone requesting a response from the patient in order to determine whether or not the patient is within the predetermined vicinity. The patient's mobile phone may also be equipped with an application, i.e., an app that provides for determining the patient's location to ensure that the patient is within the predetermined vicinity. This app may be a continuously running app or may, for example, run in connection with another program. The present invention also contemplates that social networking may be used to determine the location of the patient and that the social networking may be readily run on the patient's mobile phone. Upon receiving the phone call, the patient may be prompted to enter information to verify their location. The second controller 14 may thereafter transmit an indication to the first controller 12 in response to the first signal received from the first controller regarding whether the patient is within a predetermined vicinity of the medical facility 18 at the time that the predetermined event occurs, i.e., at the time that the medical services are being provided, based on the predetermined information entered by the patient to verify their location with respect to the medical facility.

More specifically, the predetermined information that the patient is prompted to enter to verify their location may, for example, be a predetermined patient identifier. Such a predetermined patient identifier may, for example, be a personal identification number, a predetermined code assigned to the patient, or any other type of predetermined patient identifier that may be unique to the patient or that is generally known only to the patient, as understood by those skilled in the art. Upon entering the predetermined patient identifier, the patient may also be prompted to confirm whether or not they are within the predetermined vicinity of the medical facility 18 where medical services are being provided. This may be accomplished in multiple steps, or a single step. For example, the patient may be prompted to enter the predetermined information to verify their location, as well as to verify their identity, i.e., to ensure that the patient is the one entering the predetermined patient identifier. This advantageously decreases the possibility that medical claim fraud is taking place.

Those skilled in the art will appreciate that the predetermined information is preferably unique to the patient, and it can be assumed that the patient does not share that predetermined information with others. Accordingly, entry of the predetermined information may act as verification of both the patient's location and the patient's identity. Alternately, the patient may be asked to confirm their identity and their location in separate steps. In other words, system 10 according to the present invention contemplates that the patient may be prompted to enter a first item of predetermined information to verify their identity, and a second item of predetermined information to verify their location. Of course, these pieces of information may be verified in any order, i.e., patient location may be verified prior to patient identity.

As described above, the patient may be assigned a patient information unit 22 having predetermined patient information associated therewith. The predetermined event that may prompt transmission of the first signal from the first controller 12 to the second controller 14 to initiate a telephone call to the patient's mobile phone may, for example, be reading information from the patient information unit 22 using the patient information reader 24. Additional information from the patient information unit 22 and the patient information reader 24 are provided above, and require no further discussion herein.

As also indicated above, a medical software system 26 may be positioned in communication with the first controller 12 and may be used by a medical professional at the medical facility 18. Accordingly, the predetermined event that may prompt transmission of the first signal from the first controller 12 to the second controller 14 to initiate a telephone call to a patient's mobile telephone to determine whether or not the patient is located within the predetermined vicinity of the medical facility 18 at the time that the medical services are being provided may be entry of information relating to the patient using the medical software system 26. Additional details of the medical software system 26 are provided above and require no further discussion herein.

A billing system may also be used at the medical facility 18 to bill for medical services provided to the patient. Accordingly, the predetermined event that prompts transmission of the first signal from the first controller 12 to the second controller 14 to initiate a telephone call to the patient's mobile phone to determine whether or not the patient is located within the vicinity of the medical facility may be use of the billing system with respect to the patient. As also indicated above, the signal transmitted from the first controller 12 to the second controller 14 may include information relating to a claim for reimbursement relating to medical services being provided to the patient at the medical facility 18. The second controller 14 may transmit a signal to the first controller 12 including an indication of whether or not the claim is a valid claim based on the indication of whether the patient is within the predetermined vicinity of the medical facility 18 at the time that the medical services are being provided.

As also noted above, the predetermined information that the patient is prompted to enter responsive to the telephone call to the patient's mobile telephone may, for example, be a personal identification number. The patient may enter the personal identification number using the telephone keypad. Of course, those skilled in art will appreciate that the personal identification number may be related to numerals on the telephone keypad, or may be related to letters associated with the numerals on the telephone keypad. The predetermined information that the patient is prompted to enter may also be a verbal response to a question presented to the patient. This verbal response may include the personal identification number, or some other unique identifier that may either be predetermined, or that the patient may set. Accordingly, the system 10 according to an embodiment of the present invention contemplates the use of a voice recognition system to recognize a verbal response being made by the patient in response to the presented question.

The system 10 according to the present invention contemplates that an automated system may be used to prompt the patient to enter the predetermined information, i.e., a prerecorded system adapted to recognize entry of the information from the patient and process that information using a processor to determine whether or not the patient is located within the predetermined vicinity of the medical facility 18. Alternately, a customer service representative, i.e., a live person, may initiate the telephone call, and actually speak to the patient to determine whether or not the patient is within the predetermined vicinity of the medical facility 18 at the time that medical services are being provided to the patient. If the customer service representative determines that the patient is within the predetermined vicinity of the medical facility during the time that the medical services are being provided, then the customer service representative may cause the second controller to transmit an indication to the first controller that the patient is within the predetermined vicinity of the medical facility at the time that the medical services are being provided.

As also illustrated in FIG. 10, the system 10 according to an embodiment of the present invention may advantageously include a backup patient locating system. The backup patient locating system may be activated based on an indication that the patient is not within the predetermined vicinity of the medical facility 18 at the time that the medical services are being provided. In the embodiment of the medical claim fraud prevention system 10 described above, the backup locating system included the ability to call the patient to determine if the patient is within the predetermined vicinity of the medical facility 18 at the time that the medical services are being provided (as illustrated in schematic box 31). The backup locating system in this particular embodiment can include initiating a telephone call to the medical facility 18 to speak with the patient and/or a medical professional at the medical facility to determine if the patient is located at the medical facility at the time that the medical services are being provided (as illustrated in schematic box 33). The backup locating system in this embodiment of the present invention may also include providing a notification to the medical facility 18 including a request that the patient contact the patient information collection center 20 to verify the patient's location as illustrated, for example, in schematic box 27.

Figure 11:
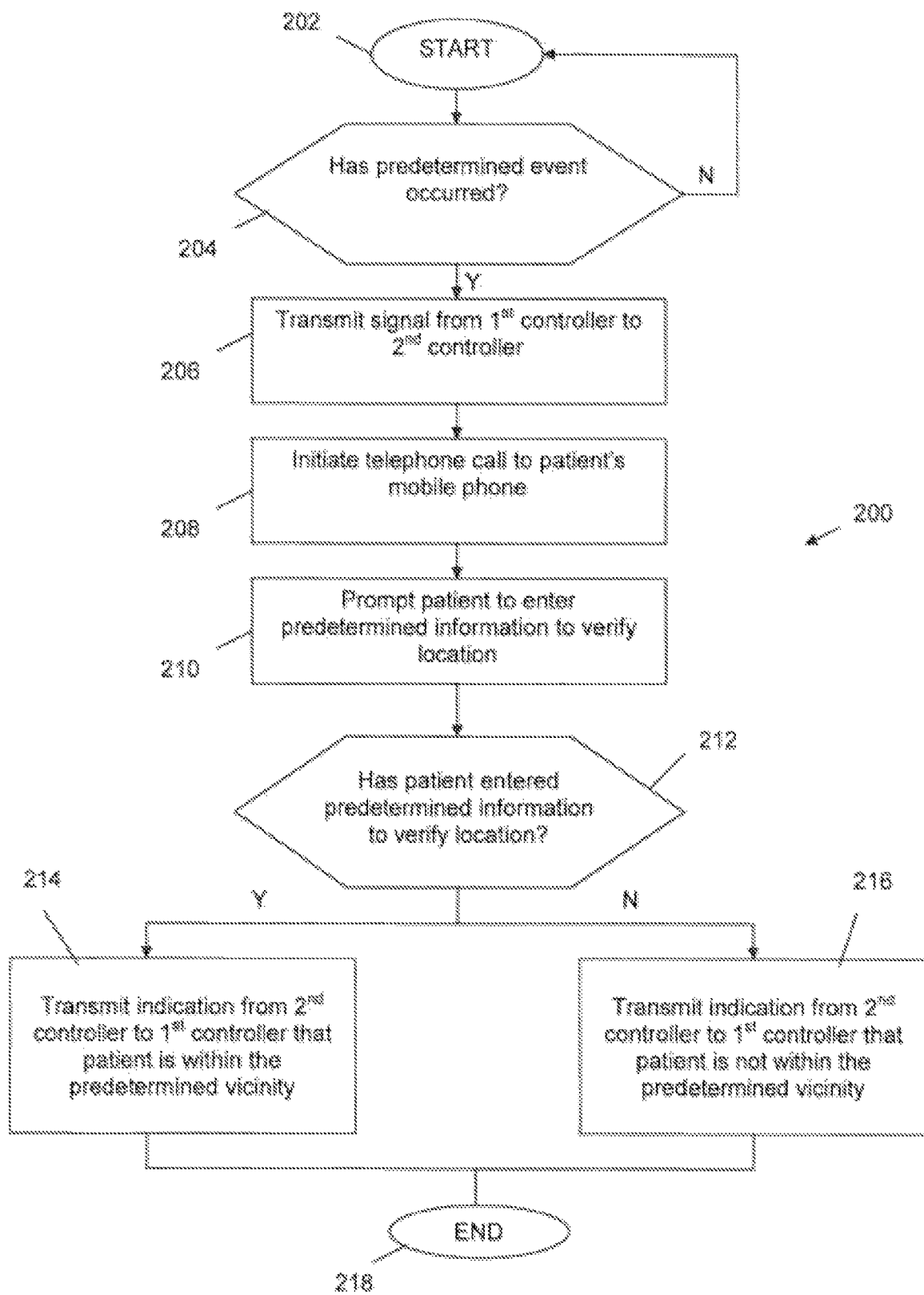
FIGS. 11-18 are flowcharts illustrating methods of prevention a medical claim fraud according to an alternate embodiment of the invention.

Referring now to the flowchart 200 illustrated in FIG. 11, a method aspect according to the present invention is now described in greater detail. The method illustrated in the flowchart 200 of FIG. 11 is directed to preventing medical claim fraud by confirming the location of the patient while the patient is at the medical facility using the patient's cell phone. More particularly, from the start (Block 202), it is determined at Block 204 if a predetermined event has occurred. If it is determined at Block 204 that the predetermined event has not occurred, then the method awaits occurrence of the predetermined event at the start Block 202. If, however, it is determined at Block 204 that the predetermined event has occurred, then a first signal is transmitted from the first controller to the second controller at Block 206.

Thereafter, at Block 208, a telephone call is initiated to the patient's mobile phone. At Block 210 the patient is prompted to enter predetermined information to verify their location. At Block 212 it is determined whether or not the patient has entered the predetermined information to verify the location. More specifically, if the patient has entered any information at all, it is determined whether or not the information entered by the patient is the predetermined information required to verify their location. If it is determined at Block 212 that the patient has entered the predetermined information necessary to verify their location, an indication is transmitted from the second controller to the first controller mat the patient is within the predetermined vicinity of the medical facility at the time that the predetermined event has occurred (wherein occurrence of the predetermined event is an indication that the medical services are being provided) at Block 214. If, however, it is determined at Block 212 that the patient has not entered the predetermined information necessary to verify their location, then an indication is transmitted from the second controller to the first controller that the patient is not within the predetermined vicinity of the medical facility at Block 216. The method is ended at Block 218.

Figure 13:
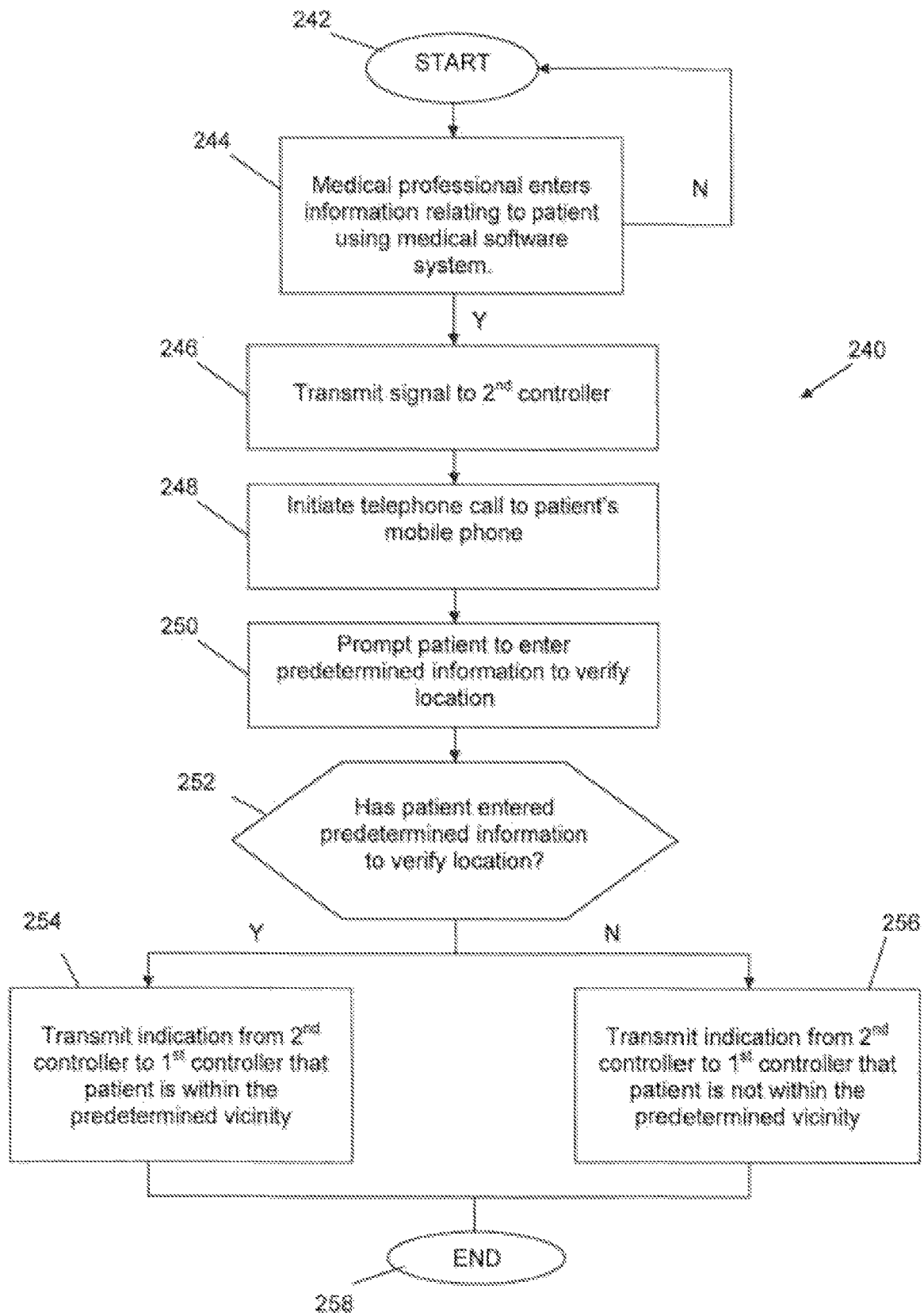

Referring now additionally to the flowchart 220 illustrated in FIG. 13, another method aspect of an embodiment of the present invention is now described in greater detail. The method aspect of the invention illustrated in the flowchart 220 of FIG. 13 illustrates that the predetermined event that prompts initiation of the telephone call to the patient's cell phone is using a patient information unit reader to read predetermined patient information from the patient information unit. From the start (Block 222), the patient information unit reader is used to read predetermined patient information from a patient information unit at Block 224. At Block 226, a first signal is transmitted to the second controller to prompt a determination of the patient's location. At Block 228, a telephone call is initiated to the patient's cell phone, and the patient is prompted to enter predetermined information to verify their location at Block 230.

Figure 12:
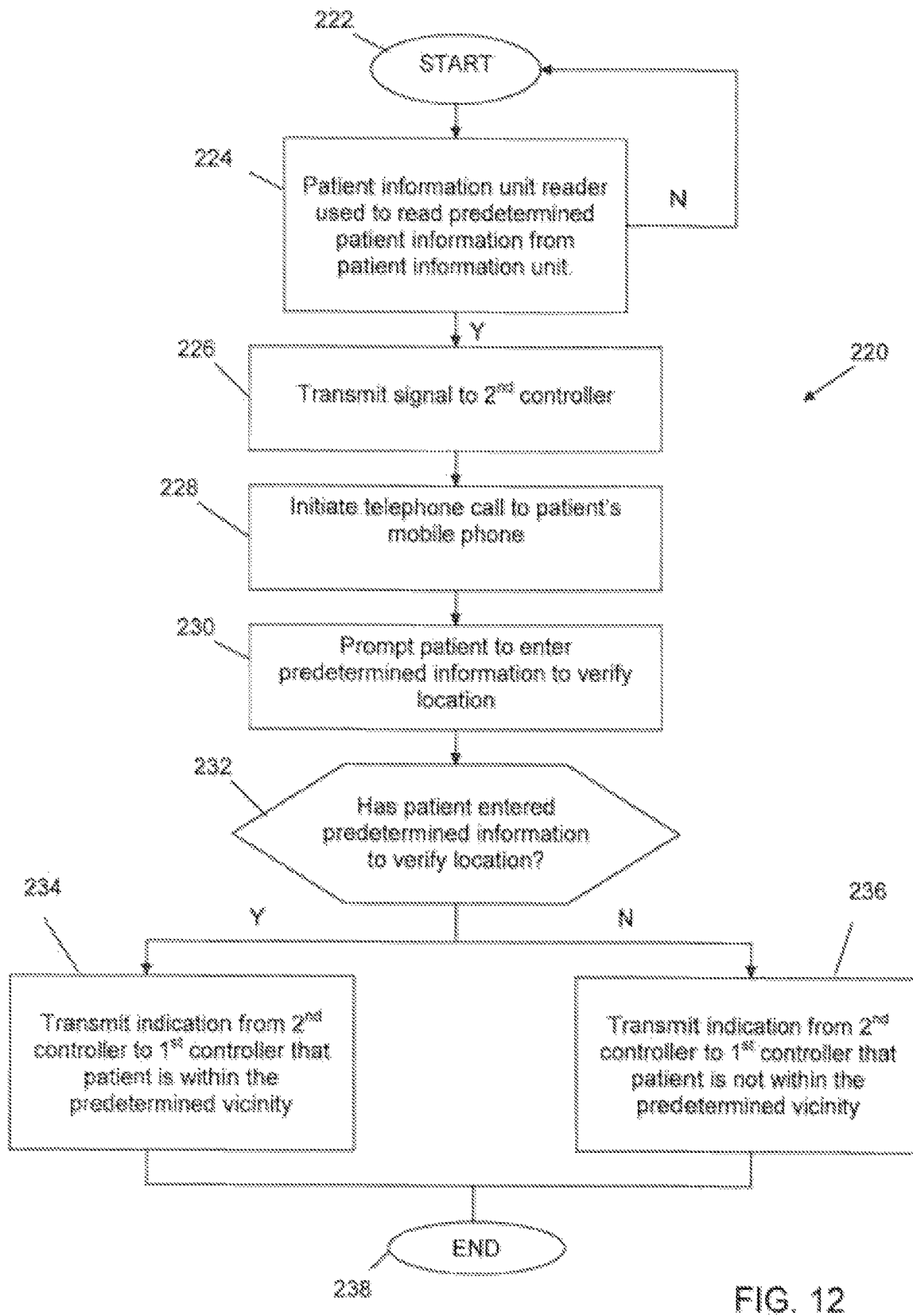

At Block 232, it is determined whether or not the patient has entered the predetermined information necessary to verify their location at the time that the medical services are being provided. If it is determined at Block 232 that the patient has entered the predetermined information necessary to verify their location then an indication is transmitted from the second controller to the first controller that the patient is within the predetermined vicinity of the medical facility at the time that the patient information unit reader is used to read predetermined patient information from the patient information unit (wherein reading information from the patient information unit is an indication that medical services are being provided to the patient) at Block 234. If, however, it is determined at Block 232 that the patient has not entered the predetermined information necessary to verify their location, then an indication is transmitted from the second controller to the first controller that the patient is not within the predetermined vicinity at the time that the patient information is read from the patient information unit using the patient information unit reader at Block 236. Accordingly, the method aspect of the invention illustrated in the flowchart 220 of FIG. 12 shows that the predetermined event that triggers determination of the patient's location is reading predetermined patient information from the patient information unit using the patient information unit reader. The method is ended at Block 238.

Referring now to the flowchart 240 illustrated in FIG. 13, still another method aspect according to an embodiment of the present invention is now described in greater detail. From the start (Block 242), a medical professional may enter information relating to the patient using a medical software system at Block 244. Thereafter, the first signal may be transmitted to the second controller at Block 246 to prompt the determination of a patient's location with respect to the medical facility. At Block 248, a telephone call may be initiated to the patient's mobile phone. At Block 250, the patient may be prompted to enter predetermined information to verify their location. At Block 252, it is determined whether or not the patient has entered the predetermined information necessary to verify their location at the time that the medical professional enters information into the medical software system relating to the patient (wherein entering information regarding the patient into the medical software system is an indication that medical services are being provided to the patient).

If it is determined at Block 252 that the patient has entered the predetermined information necessary to verify their location, then an indication is transmitted from the second controller to the first controller that the patient is within the predetermined vicinity of the medical facility at the time that the medical professional has entered information relating to the patient into the medical software system at Block 254. If, however, it is determined that the patient has not entered the predetermined information necessary to verify their location at Block 252, then an indication is transmitted from the second controller to the first controller that the patient is not within the predetermined vicinity at the time that the medical professional has entered information relating to the patient into the medical software system at Block 256. Accordingly, the method illustrated in the flowchart 240 of FIG. 13 provides that the predetermined event required to transmit the first signal from the first controller to the second controller to prompt a determination of the location of the patient with respect to the medical facility is use of a medical software system by a medical professional with respect to a patient. The method is ended at Block 258.

Figure 14:
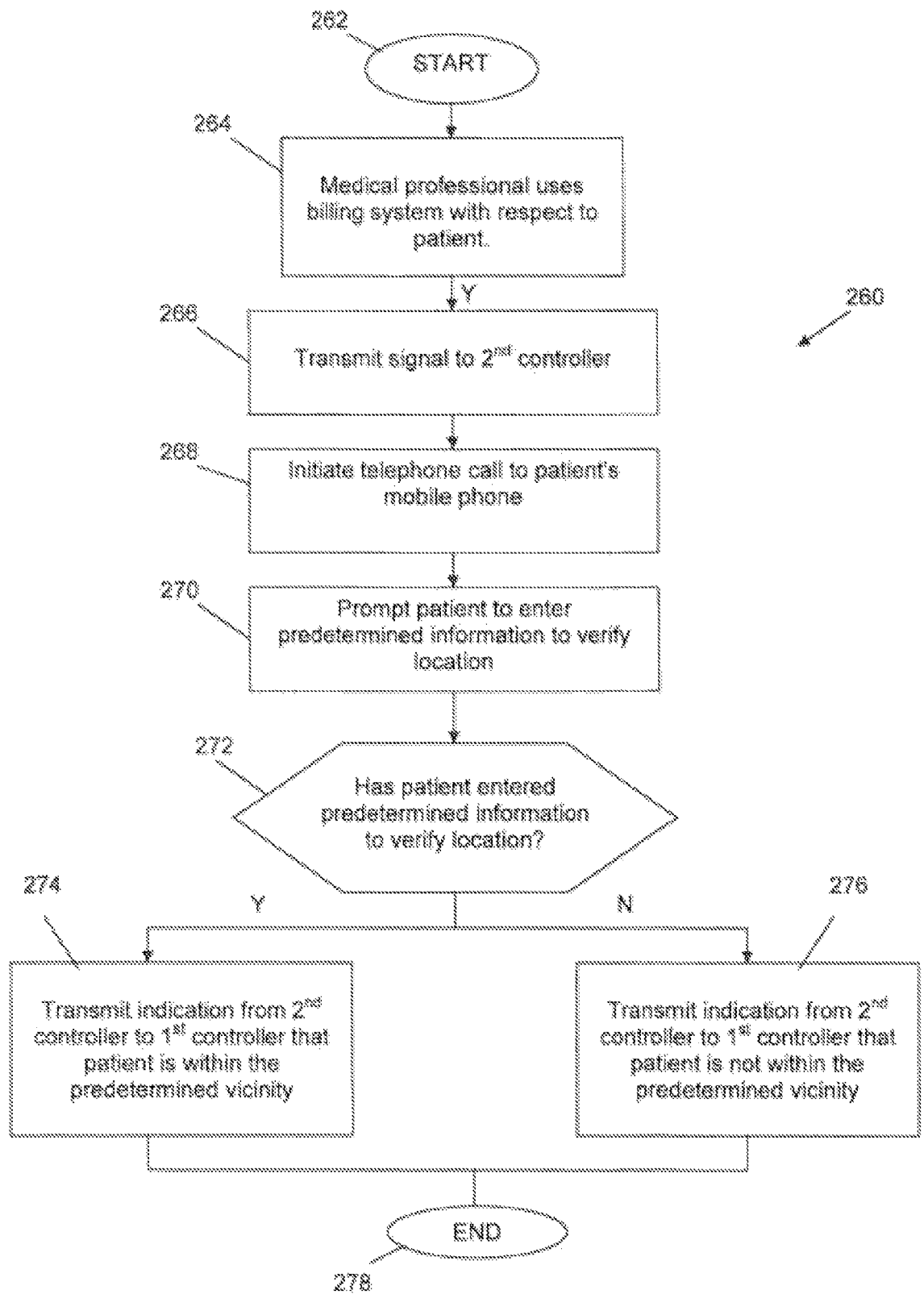

Referring now to the flowchart 260 illustrated in FIG. 14, still another method aspect of an embodiment of the present invention is now described in greater detail. From the start (Block 262), a medical professional may use a billing system with respect to a patient at Block 264. Upon use of the billing system with respect to the patient at Block 264, the first signal may be transmitted to the second controller at Block 266 to prompt a determination of the location of a patient with respect to the medical facility. At Block 268, a telephone call may be initiated to the patient's mobile phone, and at Block 270 the patient may be prompted to enter predetermined information to verify their location. It is determined at Block 272 whether the patient has entered the predetermined information necessary to verify their location at the time that the billing system is used with respect to the patient (wherein use of the billing system with respect to the patient is an indication that medical services are being provided to the patient).

If it is determined at Block 272 that the patient has entered the predetermined information necessary to verify their location, then an indication is transmitted from the second controller to the first controller that the patient is within the predetermined vicinity of the medical facility at the time that the billing system is used with respect to the patient at Block 274. If, however, it is determined that the patient has not entered the predetermined information necessary to verify their location at Block 272 then an indication is transmitted from the second controller to the first controller that the patient is not within the predetermined vicinity at the time that the billing system is used with respect to the patient at Block 276. Accordingly, the method aspect of the invention illustrated in the flowchart 260 of FIG. 14 provides that the predetermined event that prompts the determination of the location of the patient is using a billing system with respect to the patient. The method is ended at Block 278.

Figure 15:
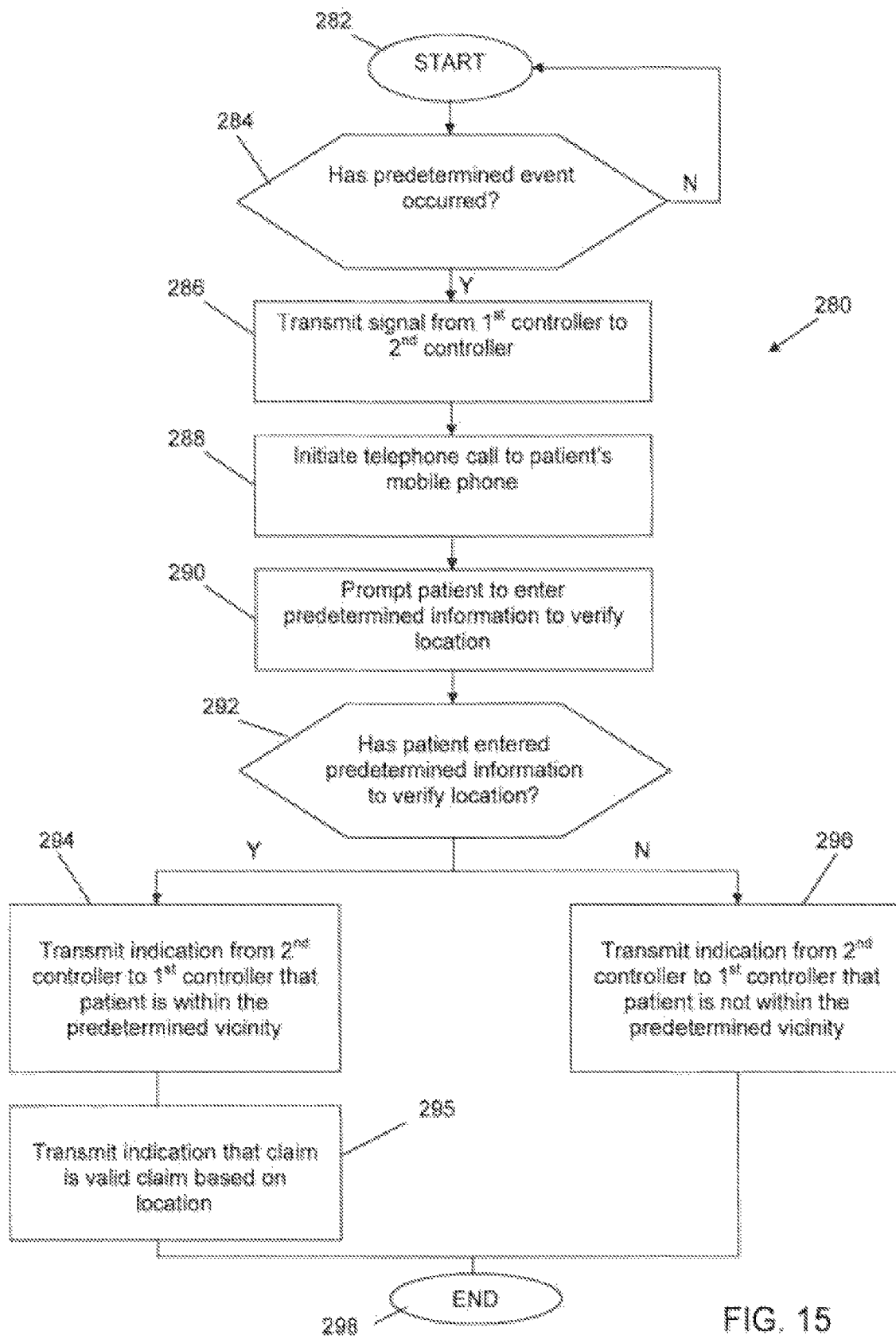

Referring now additionally to the flowchart 280 illustrated in FIG. 15, another method aspect of an embodiment of the present invention is now described in greater detail. The method aspect of the invention illustrated in the flowchart 280 of FIG. 15 includes steps to automatically request reimbursement for medical services being provided to the patient, and further includes transmitting a signal of whether or not the request for reimbursement of medical expenses associated with the medical services being provided to the patient are approved based on an indication of the patient's location with respect to the medical facility at the time the predetermined event occurs (wherein occurrence of the predetermined event is an indication that the medical services are being provided to the patient). From the start (Block 282), it is determined at Block 284 if a predetermined event has occurred. If it is determined at Block 284 that the predetermined event has not occurred, then the method awaits occurrence to the predetermined event at the start Block 282. If, however, it is determined that the predetermined event has occurred at Block 284, then a first signal is transmitted from the first controller to the second controller at Block 286 to prompt a determination of the location of the patient at Block 286. The first signal may include information relating to a request for reimbursement of medical services being provided to the patient.

Thereafter, a telephone call may be initiated to the patient's mobile phone at Block 288, and the patient may be prompted to enter predetermined information to verify their location at the time that the medical services are being provided at Block 290. At Block 292 is it determined whether or not the patient has entered the predetermined information necessary to verify their location at the time that the medical services are being provided, i.e., at the time of the occurrence of the predetermined event.

If it is determined at Block 294 that the patient has entered the predetermined information necessary to verify their location, then an indication may be transmitted from the second controller to the first controller that the patient is within the predetermined vicinity of the medical facility upon the occurrence of the predetermined event at Block 294. Along with the signal transmitted from the second controller to the first controller may be an indication that a claim of reimbursement of medical services is valid based on the location of the patient being within the predetermined vicinity of the medical facility at the time that the predetermined event occurs at Block 295. If, however, it is determined at Block 292 that the patient has not entered the predetermined information necessary to verify their location then an indication may be transmitted from the second controller to the first controller that the patient is not within the predetermined vicinity at the time that the predetermined event occurs. Accordingly, by implication, the request for reimbursement of medical services to be provided to the patient will be necessarily denied. Thereafter, the method is ended at Block 298.

Similar to the embodiment of the medical claim fraud prevention system 10 described above, this embodiment of the medical claim fraud prevention system also includes a backup locating system. More specifically, I am referring now to the flow chart 450 illustrated in FIG. 16, a method aspect of an embodiment of the present invention relating to the backup locating system is now described in greater detail. From the start (Block 452), it is determined at Block 454 whether or not an indication has been transmitted from the second controller to the first controller indicating that the patient is not within the predetermined vicinity of the medical facility. If it is determined at Block 454 that an indication has not been transmitted from the second controller to the first controller indicating that the patient in not within the predetermined vicinity of the medical facility, then the method is ended at Block 459. If, however, it is determined at Block 454 that an indication has been transmitted from the second controller to the first controller indicating that the patient is not within the predetermined vicinity of the medical facility, then the backup locating system is activated at Block 456. At Block 458, a patient's mobile telephone is called to determine the location of the patient. The method is thereafter ended at Block 459.

Figure 17:
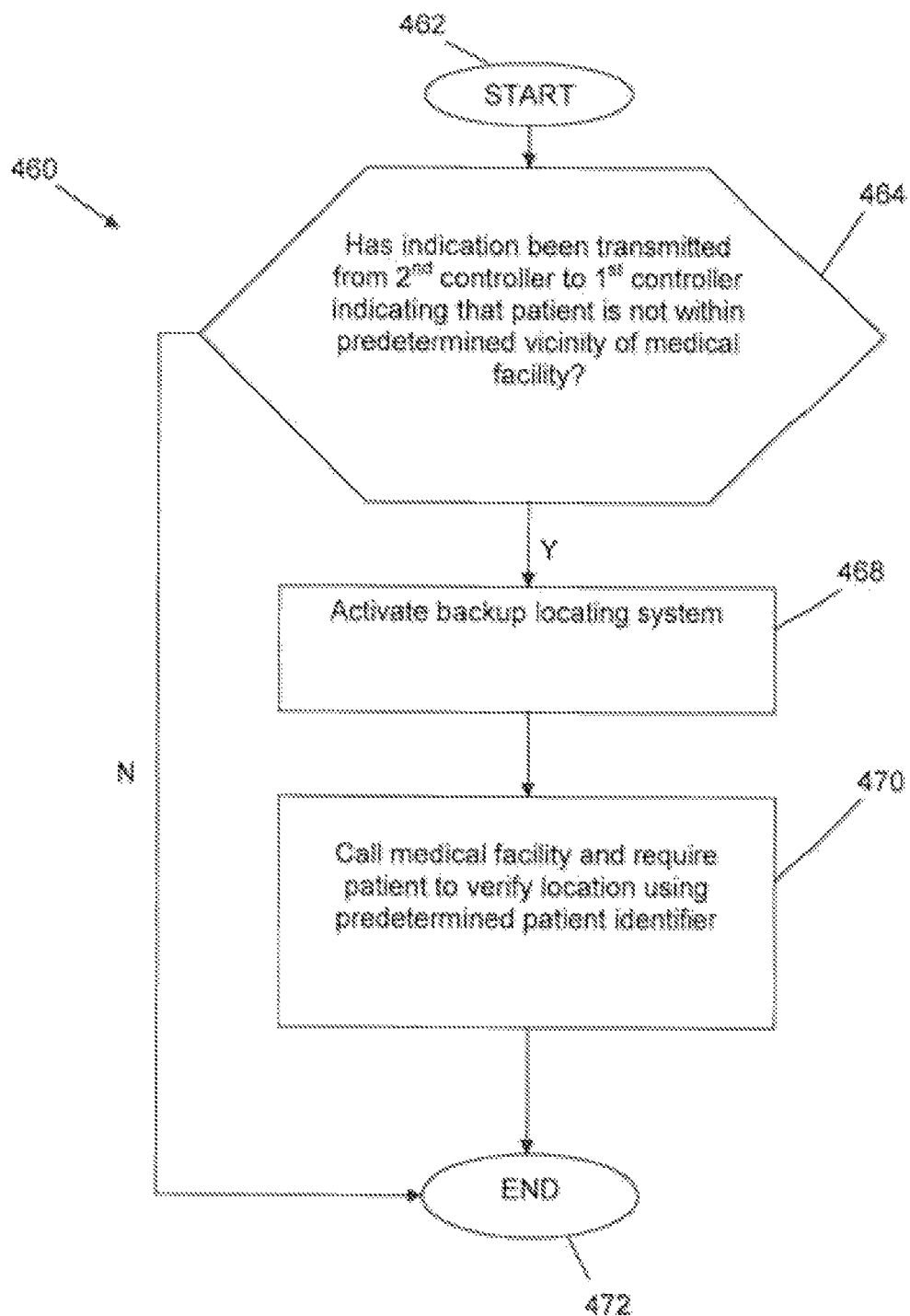

Referring now additionally to the flow chart 460 illustrated in FIG. 17, additional details of the backup locating system according to this embodiment of the present invention are now described in greater detail. From the start (Block 462), it is determined at Block 464 if an indication has been transmitted from the second controller to the first controller indicating that the patient is not within the predetermined vicinity of the medical facility. If it is determined at Block 464 that such an indication has not been transmitted, then the method is ended at Block 472. If, however, it is determined at Block 464 that such an indication has been transmitted, then the backup locating system is activated at Block 468. At Block 470, the medical facility is called and the patient is required to verify their location using a predetermined patient identifier. Thereafter, the method is ended at Block 472.

Figure 18:
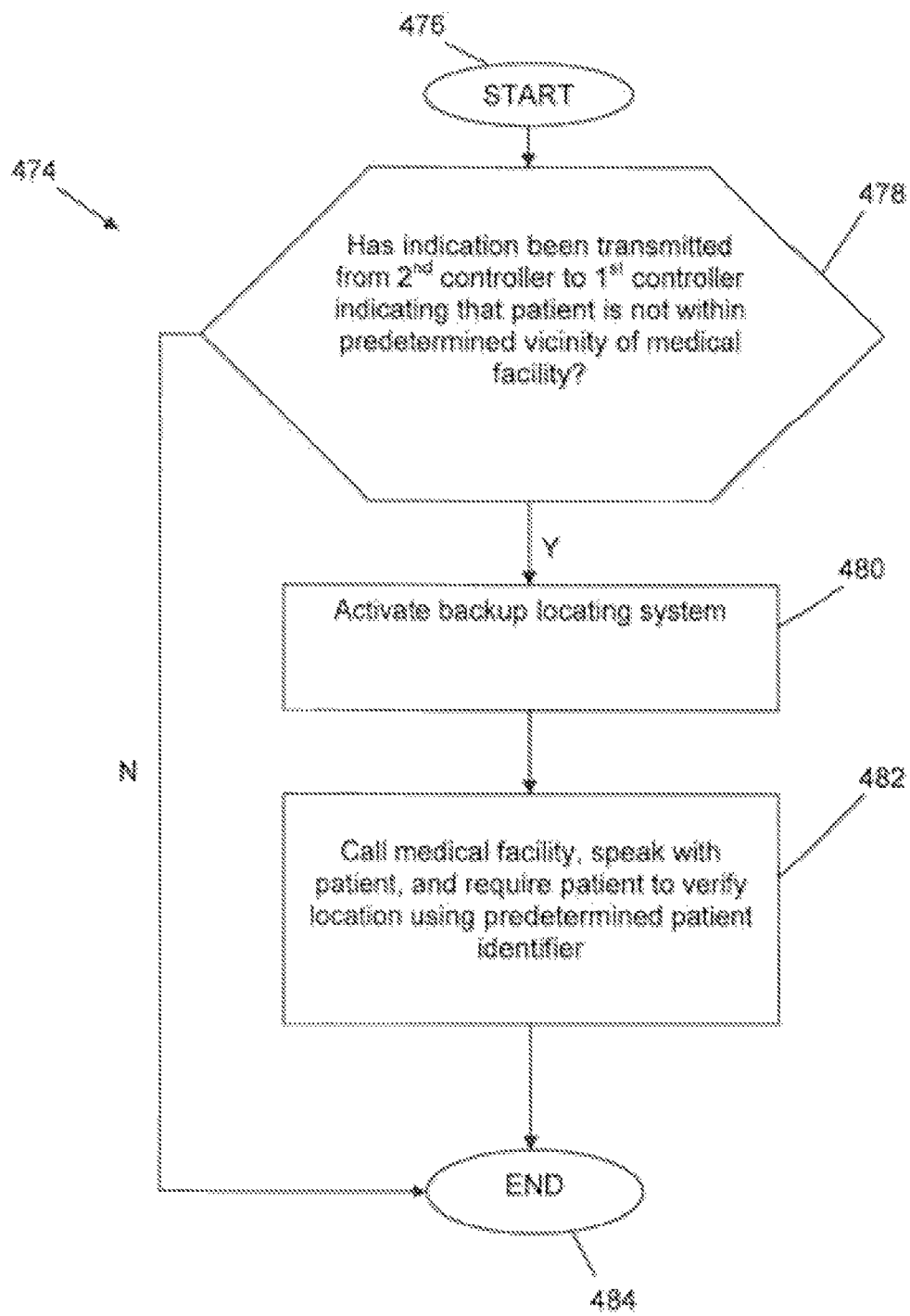

Referring now additionally to the flow chart 474 illustrated in FIG. 18, still additional features of the backup locating system according to this embodiment of the invention are now described in greater detail. From the start (Block 476), it is determined whether or not an indication has been transmitted from the second controller to the first controller indicating that the patient is not within the predetermined vicinity of the medical facility at Block 478. If it is determined that such an indication has not been transmitted at Block 478, then the method is ended at Block 484. If, however, it is determined that such an indication has been transmitted at Block 478, then the backup locating system is activated at Block 480. Thereafter, the medical facility may be called, and the patient may be spoken with and required the patient to verify their location using a predetermined patient identifier that may be verbally provided at Block 482. Thereafter, the method is ended at Block 484.

Referring now additionally to FIG. 9, yet another embodiment of the medical claim fraud prevention system 10 according to the present invention is now described in greater detail. This embodiment of the medical claim fraud prevention system 10 confirms the location of a patient using a user interface 28 associated with the first controller 12 positioned at the medical facility 18. More specifically, and similar to the other embodiments of the medical claim fraud prevention system 10, this embodiment of the system includes a first controller 12 positioned at the medical facility 18. The first controller 12 of this embodiment of the system 10 may include a user interface 28 or, alternately, may be positioned in communication with the user interface. The second controller 14 may be positioned at the patient information collection center 20 and adapted to be in communication with the first controller 12. There may be another user interface at the patient informant collection center 20 that is adapted to be used by a user to communicate with the first controller and, more specifically, with the medical professional at the medical facility 18 or with the patient. The second controller 14 may include the user interface or, alternately, may be in communication with the user interface. The first controller 12 may transmit a first signal to the second controller 14 responsive to the occurrence of a predetermined event.

Thereafter, the second controller 14 may request identification information from the patient in response to the first signal received from the first controller 12. As illustrated in the schematic box 491, the patient may enter the identification information using the user interface 28 in communication with the second controller 14 to verify the patient's location. The second controller 14 may transmit an indication to the first controller 12 in response to the first signal received from the first controller regarding whether the patient is within the predetermined vicinity of the medical facility 18 based on the identification information entered by the patient using the user interface 28 to verify their location. In other words, if the patient has not entered the necessary identification information into the user interface 28, or if the patient has entered incorrect identification information into the user interface, then the second controller 14 may transmit a signal to the first controller 12 that the patient is not within the predetermined vicinity of the medical facility 18. If, however, the patient has entered the proper identification information into the user interface 28, then an indication may be transmitted from the second controller 14 to the first controller 12 that the patient is within the predetermined vicinity of the medical facility 18.

Similar to other embodiments of the medical claim fraud prevention system 10 according to the present invention, this embodiment of the system contemplates that the patient may be assigned a patient information unit 22 having predetermined patient information associated therewith, and that the predetermined event for prompting the first controller 12 to send the first signal to the second controller 14 to request that the patient enter identification information using the user interface 28 may be reading information from the patient information unit 22 using the patient information unit reader 24. Additional details of the patient information unit 22 and using the patient information unit reader 24 to determine whether or not the patient is located within a predetermined vicinity of the medical facility 18 at the time that the medical services are being provided according to the present invention are provided above, and require no further discussion herein.

Similar to the embodiment of the medical claim fraud prevention system 10 described above, the identification information to be entered by the patient may be a personal identification number. The personal identification number may be a series of numerals, words, letters, or any combination thereof that may be entered using the interface 28 located at the medical facility 18. Also similar to alternate embodiments of the medical claim fraud prevention system 10 according to the present invention, the patient information collection center 20 may be associated with processing health insurance claims, and the signal transmitted from the first controller 12 to the second controller 14 may include information relating to a claim for reimbursement relating to medical services being provided to the patient at the medical facility 18. The second controller 14 may transmit a signal to the first controller 12 including an indication as to whether or not the claim is a valid claim based on the indication of whether the patient is within the predetermined vicinity of the medical facility 18 at the time that the medical services are being provided.

Accordingly, this embodiment of the medical claim fraud prevention system 10 according to the present invention allows for the patient to enter identification information using the user interface 28 located at the medical facility to verify the patient's location. Similar to other embodiments of the medical claim fraud prevention system 10 according to the present invention, this embodiment of the system may prompt the patient to enter both identification information, and verification information that the patient is located at the medical facility 18 at the time that medical services are being provided. The user interface 28 may, for example, be provided by a computer located at the medical facility 18. The user interface 28 may also be provided by any other device capable of transmitting identification information of the patient so that the location of the patient may be verified. Other examples may, for example, be a handheld user interface, a touch screen monitor, a keypad, or any other type of user interface suitable to allow a patient to enter identification information to verify their location.

Figure 19:
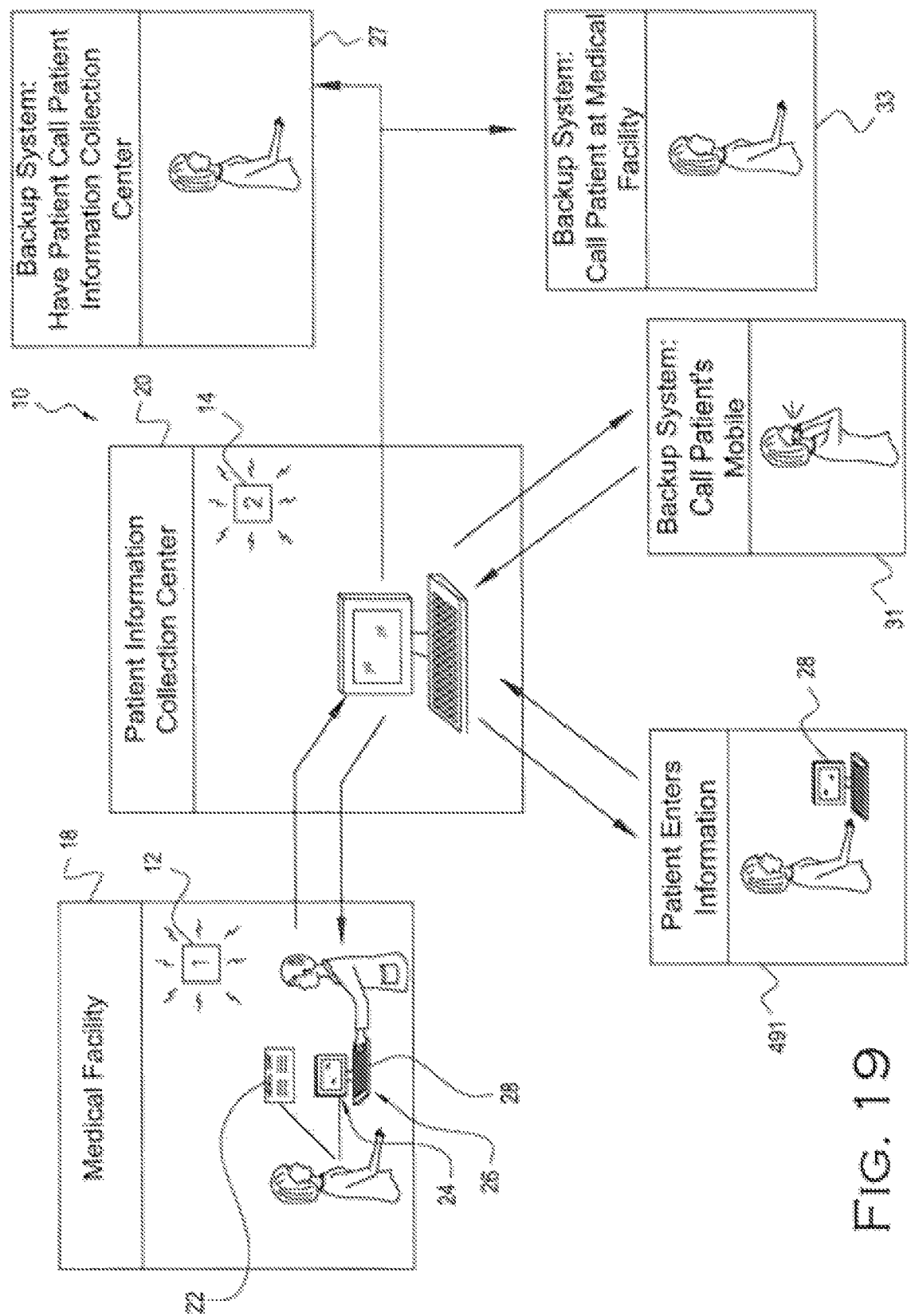
FIG. 19 is a schematic environmental view of an alternate embodiment of the medical claim fraud prevention system according to the present invention.

As further illustrated in FIG. 19, this embodiment of the medical claim fraud prevention system 10 may include a backup locating system to locate the patient in the case where attempts to locate the patient using the user interface positioned at the medical facility 18 falls. As illustrated in schematic Box 31, the backup locating system may provide for calling the patient to determine if the patient is located at the medical facility 18 at the time that the medical services are being provided or, as illustrated in schematic box 33, calling the medical facility to speak with the patient to determine if the patient is at the medical facility at the time that the medical services are being provided. When calling the patient to determine if the patient is at the medical facility 18 at the time that the medical services are being provided, the patient may be called on his/her cell phone or may be called at the medical facility. Further, the patient may be prompted to enter a predetermined identification code using the keypad of either the patient's cell phone or the keypad of the telephone at the medical facility. The patient may also be prompted to provide some identifying information to verify the patient's identity verbally to a customer service representative. The backup locating system in this embodiment of the present invention may also include providing a notification to the medical facility 18 including a request that the patient contact the patient information collection center 20 to verify the patient's location as illustrated, for example, in schematic box 27.

Figure 20:
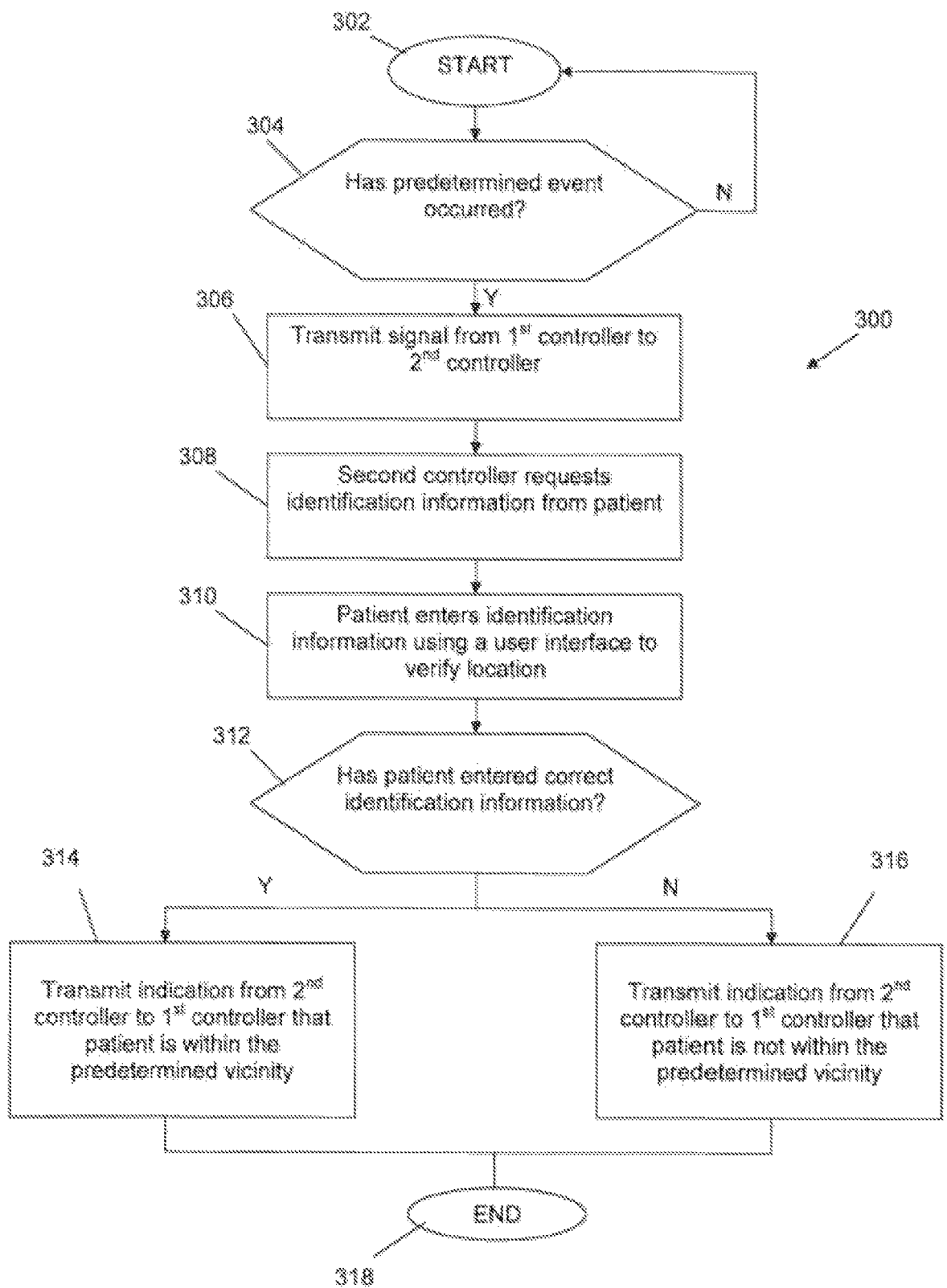
FIGS. 20-22 are flowcharts illustrating methods of prevention a medical claim fraud according to an alternate embodiment of the invention.

Referring now additionally to the flowchart 300 illustrated in FIG. 20, a method aspect of an embodiment according to the present invention is now described. The following flowcharts are directed to an embodiment of the invention in which a method is provided for confirming the location of a patient by prompting the patient to enter information using a user interface. More specifically, from the start (Block 302), it is determined at Block 304 if a predetermined event has occurred. If it is determined at Block 304 that the predetermined event has not occurred, then the method awaits the predetermined event to occur at the start Block 302. If, however, it is determined at Block 304 that the predetermined event has occurred, then a first signal is transmitted from the first controller to the second controller at Block 306.

At Block 308, the second controller requests identification information be inputted from the patient into the user interface. At Block 310, the patient enters identification information using a user interface to verify their location at the time that the predetermined event occurs (wherein occurrence of the predetermined event is presumed to be an indication of the time at which medical services are being provided to the patient). At Block 312 it is determined whether or not the patient has entered the correct identification information necessary to verify their location at the time that the predetermined event has occurred. If it is determined at Block 312 that the patient has entered the appropriate identification information, then an indication may be transmitted from the second controller to the first controller that the patient is within the predetermined vicinity of the medical facility at the time that the predetermined event occurred at Block 314. If, however, it is determined at Block 312 that the patient has not entered the appropriate identification information to verify their location, then an indication is transmitted from the second controller to the first controller that the patient is not within the predetermined vicinity of the medical facility at the time that the predetermined event occurred at Block 316. The method is ended at Block 318.

Figure 21:
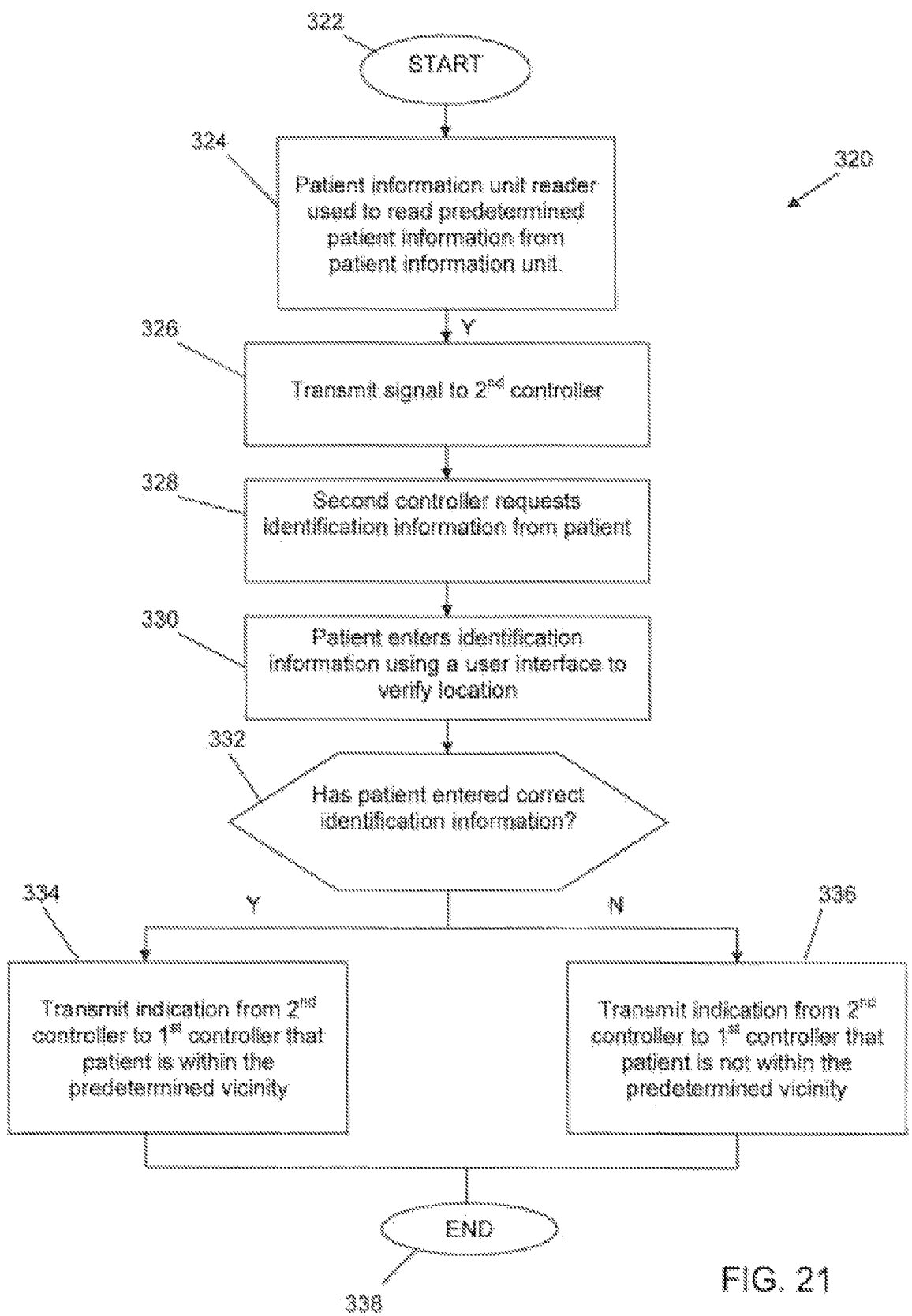

Referring now additionally to the flowchart 320 illustrated in FIG. 21, another method aspect of an embodiment of the present invention is described in greater detail. The method illustrated in the flowchart 320 of FIG. 21 prompts the first signal to be transmitted based on use of a patient information unit reader to read predetermined patient information from a patient information unit. More specifically, from the start (Block 322), a patient information unit reader is used to read the predetermined information from the patient information unit at Block 324. At Block 326, a first signal is transmitted to the second controller to prompt a determination of the location of the patient.

At Block 328, the second controller requests identification information may be entered by the patient using the user interface. At Block 330, the patient may enter the identification information requested in Block 328 using a user interface to verify their location. At Block 332, it is determined whether or not the patient has entered appropriate identification information necessary to determine whether or not the patient is within the predetermined vicinity of the medical facility at the time that the patient information unit reader is used to read the predetermined information from the patient information unit (wherein using the patient information unit reader to read the predetermined information from the patient information unit is an indication that medical services are being provided to the patient). If it is determined at Block 332 that the patient has entered the appropriate identification information, then an indication is transmitted from the second controller to the first controller that the patient is within the predetermined vicinity of the medical facility at the time that the patient information unit reader is used to read the predetermined information from the patient information unit at Block 334. If, however, it is determined that the patient has not entered the appropriate identification information at Block 332, then an indication is transmitted from the second controller to the first controller that the patient is not within the predetermined vicinity of the medical facility at the time that the patient information unit reader is used to read the predetermined information from the patient information unit at Block 336. Thereafter, the method is ended at Block 338.

Figure 22:
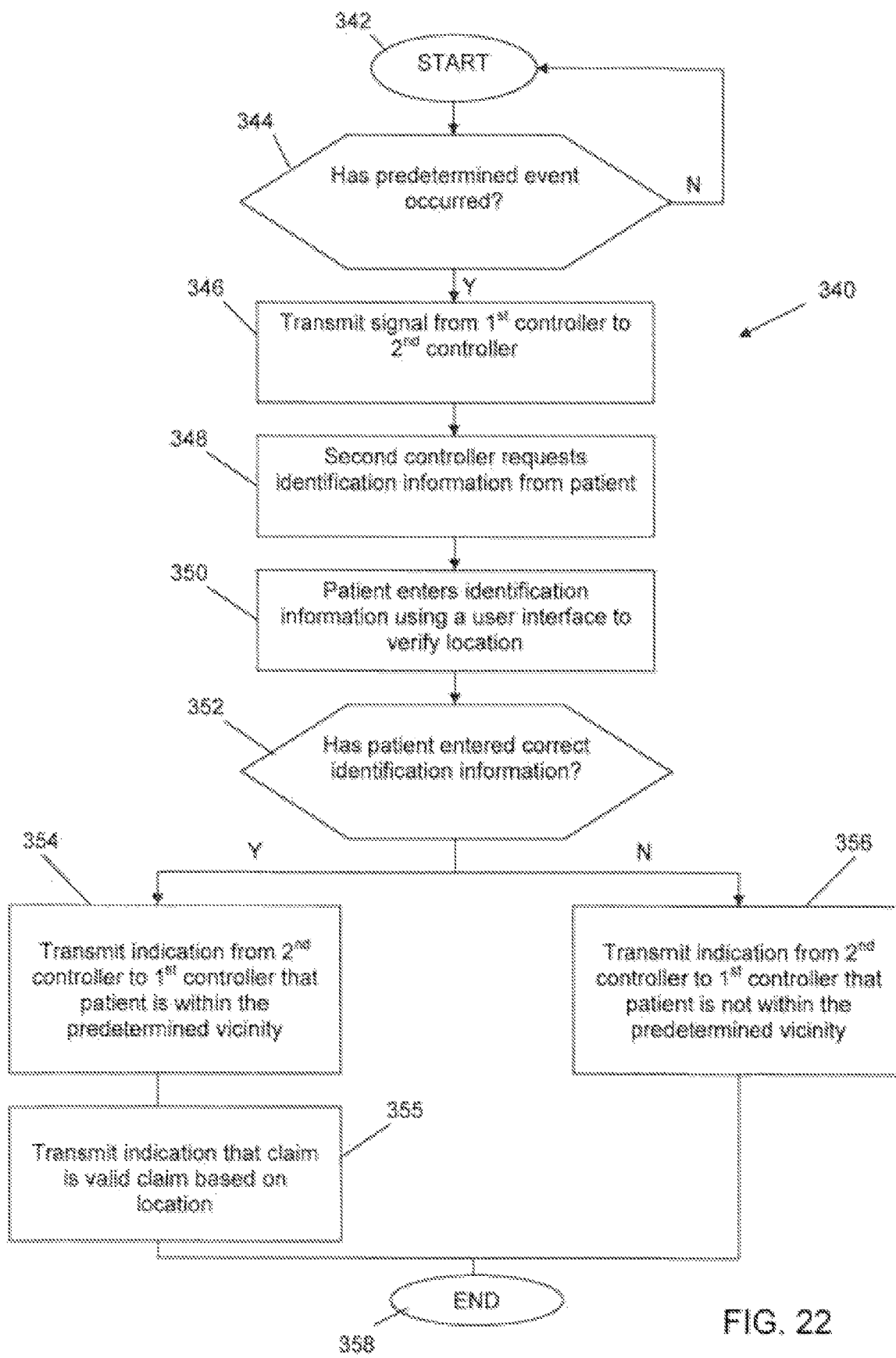

Referring now additionally to the flowchart 340 illustrated in FIG. 22, still another method aspect according to an embodiment of the present invention is now describer in greater detail. The method illustrated in the flowchart 340 illustrated in FIG. 22 provides for the ability to transmit a request for reimbursement for the provision of the medical services when transmitting the first signal from the first controller to second controller, and also provides for transmitting an indication back to the first controller that a claim is valid or invalid based on the determination of the location of the patient at the time that the medical services are being provided.

More specifically, from the start (Block 342), ft is determined whether or not the predetermined event has occurred at Block 344. If the predetermined event has not occurred at Block 344, then the method awaits for the predetermined event to occur at the start Block 342. If, however, it is determined that the predetermined event has occurred at Block 344, then the first signal is transmitted from the first controller to the second controller at Block 346. The first signal may also include a request for reimbursement of medical services being provided to the patient from the insurance company. At Block 348, the second controller requests identification information be entered by the patient, and the patient may use a user interface at the medical facility to enter the identification information at Block 350.

At Block 352, it is determined whether or not the patient has entered the appropriate identification information to verify their location within the predetermined vicinity of the medical facility. If it is determined at Block 352 that the patient has entered the appropriate identification information, then an indication is transmitted from the second controller to the first controller that the patient is within the predetermined vicinity of the medical facility at the time that the medical services are being provided at Block 354. At Block 355, an indication that the claim is valid may be transmitted based on the location of the patient. If, however, it is determined at Block 352 that the patient has not entered the appropriate identification information, then an indication may be transmitted from the second controller to the first controller that the patient is not within the predetermined vicinity of the medical facility at the time that the medical services are being provided at Block 356. The method may be ended at Block 358.

Figure 16:
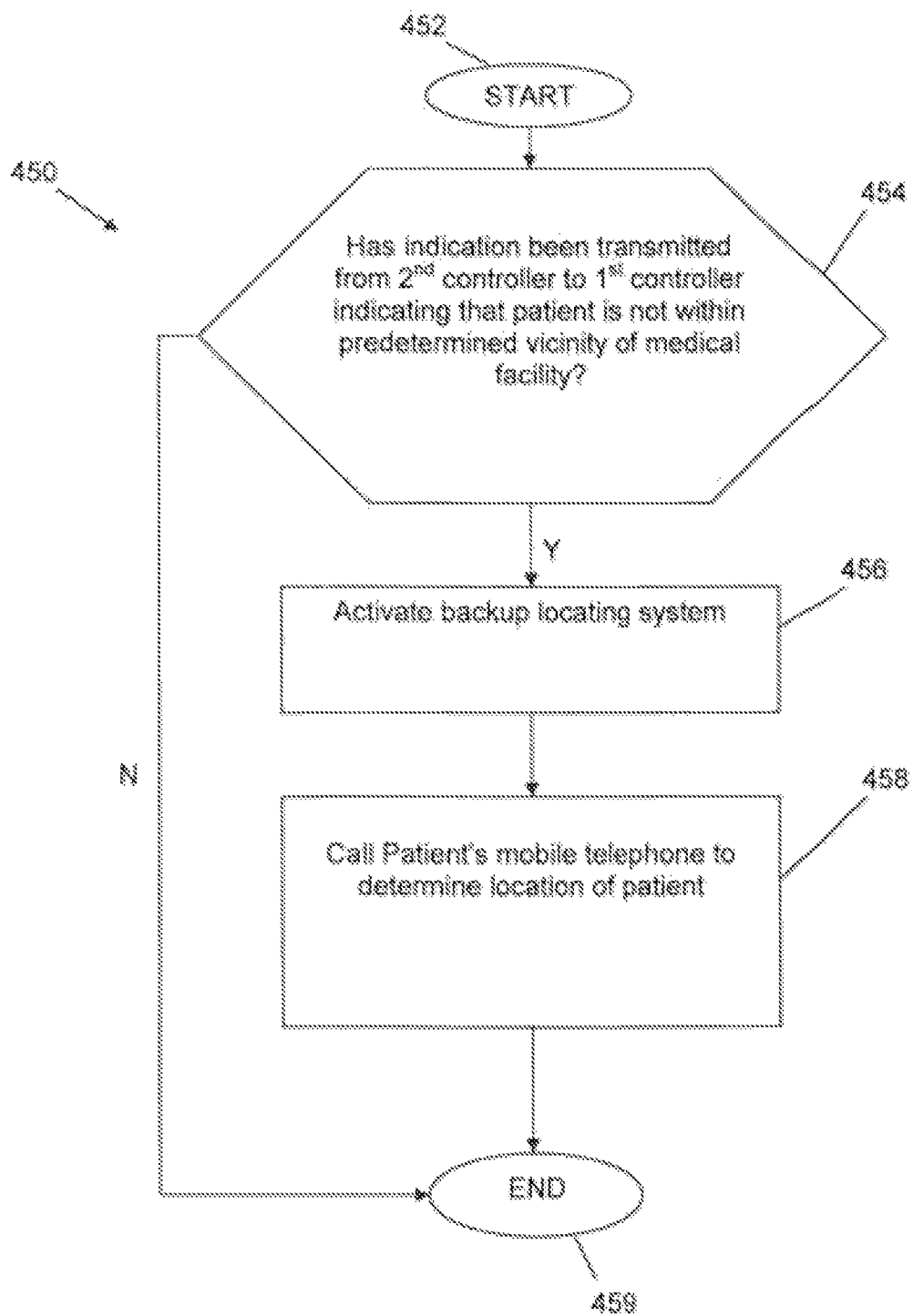

This embodiment of the invention also includes a method aspect associated with the backup locating system that is indicated above and that is illustrated in FIG. 19. The method aspect of the backup locating system according to an embodiment of the present invention is illustrated in the flowcharts of FIGS. 16-18, and described in greater detail above.

Figure 23:
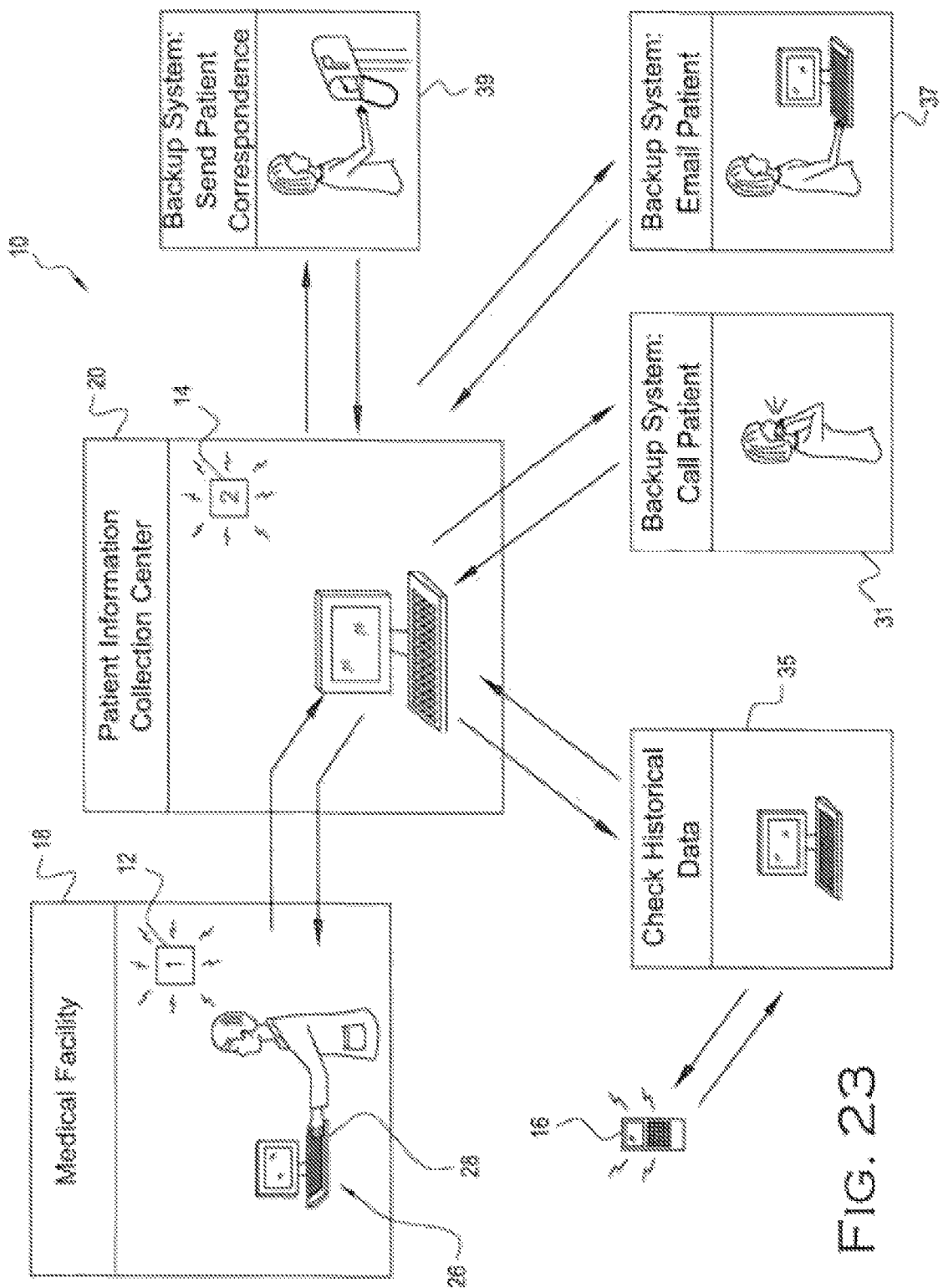
FIG. 23 is a schematic environmental view of an alternate embodiment of the medical claim fraud prevention system according to the present invention.
Figure 24:
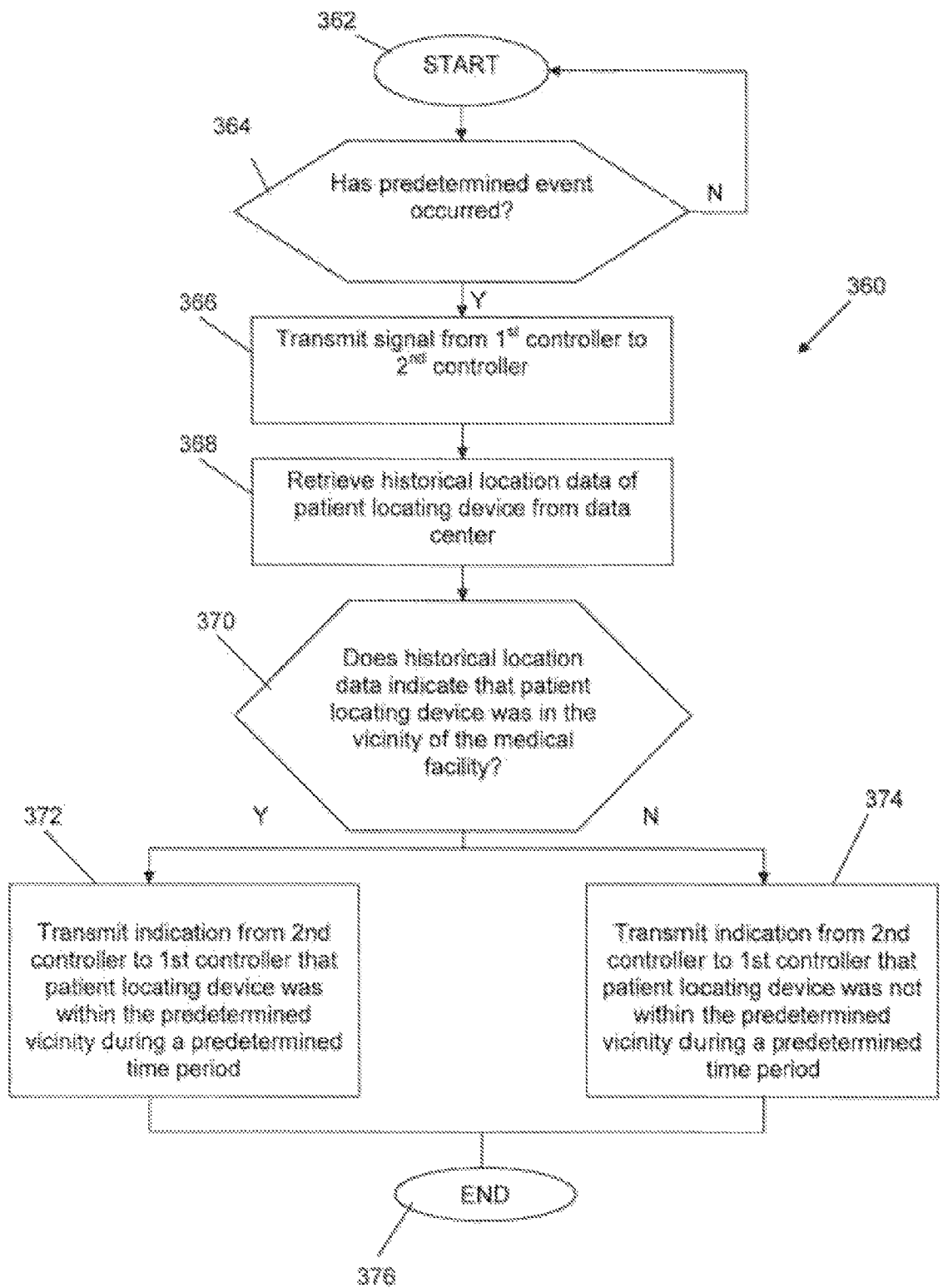
FIGS. 24-29 are flowcharts illustrating methods of prevention a medical claim fraud according to an alternate embodiment of the invention.

Referring now additionally to FIG. 23, still another embodiment of the medical claim fraud prevention system 10 according to the present invention is now described in greater detail. This embodiment of the medical claim fraud prevention system 10 advantageously confirms the location of the patient after the patient has left the medical facility 18 using historical information (as illustrated in schematic box 35) relating to location of a patient locating device 16. This advantageously allows for the location of the patient to be verified within a predetermined vicinity of the medical facility 18 during a predetermined time period, i.e., after the medical services have been provided to the patient, and after the patient has left the medical facility 18.

Similar to the other embodiments of the medical claim fraud prevention system 10, this embodiment of the system according to the present invention includes a first controller 12 positioned at the medical facility 18, and a second controller 14 positioned at a patient information collection center 20 and adapted to be in communication with a data center having a historical location information relating to the patient locating device 16, as well as in communication with the first controller. The first controller 12 may send a first signal to the second controller 14 responsive to an occurrence of a predetermined event. The second controller 14 may transmit an indication to the first controller 12 in response to the first signal received from the first controller 12 regarding the historical location of the patient locating device 16 and whether the patient locating device was within a predetermined vicinity of the medical facility 18 during a predetermined time period.

Use of a billing system at the medical facility 18 to bill for medical services provided to the patient may, for example, be the predetermined event that prompts retrieval of historical location information relating to the patient locating device 16 to determine if a patient was within a predetermined vicinity of the medical facility 18 during a predetermined time period. More particularly, it is common for a medical professional to use a billing system to ensure that patients are billed for medical services that are provided. The billing system may be used to input billing information relating to the patient after the medical services have been provided to the patient and, in many instances, after the patient has left the medical facility 18. In many instances, one medical professional may use the billing system to enter billing information relating to several patients at the same time. Accordingly, the system 10 according to the present invention contemplates retrieving historical location data relating to several different patient locating devices 16 as billing information relating to the corresponding patients is entered into the billing system.

The present invention also contemplates that the predetermined event upon which the first controller 12 transmits the first signal to the second controller 14 to retrieve historical location data of the patient locating device 16 may also be used with any medical software system 26 with respect to the patient. For example, a medical professional may have notes written on a chart relating to treatment of a patient that may be transcribed into a digital format using a medical software system 26. Upon transcribing the written comments of the medical professional on the medical chart and inputting those comments into the medical software system with respect to the patient, the first controller 12 positioned at the medical facility may transmit the first signal to the second controller 14 to retrieve historical location data of the patient locating device 16 to determine if the patient locating device was within the predetermined vicinity 18 of the medical facility during the predetermined time period. Of course, those skilled in the art will appreciate that the predetermined time period would have to be defined by the medical professional, or any other user when entering information into either the billing system, or the medical software system. Thereafter, the predetermined time period may be cross-referenced with the historical location data retrieved from the data center and relating to the location of the patient locating device 16.

As described in greater detail above, the patient locating device 16 may be a GPS enabled mobile telephone, or any GPS enabled device that allows for a determination of the location thereof, and that may also be in communication with the data center that records historical location. For example, the data center may record various locations in which the patient locating device 16 has been located and the times at which the patient locating device was moved between locations. Those skilled in the art will appreciate that the historical location data of the patient locating device 16 may be stored in any number of ways, and may be manipulated in any number of ways to provide various types of location data of the patient locating device 16. The patient locating device 16 may be any signal transmitting device capable of being triangulated to determine location data. Additional details of the patient locating device 16 are described above, and require no further discussion herein.

Similar to other embodiments of the medical claim fraud prevention system 10, this embodiment of the system according to the present invention allows for the first signal being transmitted from the first controller 12 to the second controller 14 to include information relating to a claim for reimbursement relating to medical services provided to the patient at the medical facility 18. Accordingly, the second controller 14 may transmit a signal to the first controller 12 including an indication of whether or not the claim is a valid claim based on the indication of whether the patient locating device was within the predetermined vicinity of the medical facility 18 during the predetermined time period. Additional details of validating a claim for medical reimbursement are provided above and require no further discussion herein.

As also described above with respect to other embodiments of the medical claim fraud prevention system 10, this embodiment of the system includes a backup locating system as further illustrated, for example, in FIG. 23. The backup locating system may be activated to perform a predetermined action based on a predetermined backup event. For example, the predetermined backup event that may activate the backup locating system may be an indication received from the second controller 14 that the patient locating device 16 was not within the predetermined vicinity of the medical facility 18 during the predetermined time period. As indicated above, the predetermined action taken by the backup system may be calling the mobile telephone of the patient, as illustrated in schematic box 31 and speaking with the patient to determine if the patient was within the predetermined vicinity of the medical facility 18 during the predetermined time period. Additional details of calling the patient as the predetermined action of the backup system are described in greater detail above, and require no further discussion herein.

As illustrated in schematic box 37, the predetermined action of the backup locating system may be sending the patient an e-mail that requests entry of information to verify if the patient was within the predetermined vicinity of the medical facility 18 during the predetermined time period. As further illustrated in schematic box 39, another predetermined action that may be taken by the backup locating system may be sending correspondence to the patient that requests verification of whether the patient was within the predetermined vicinity of the medical facility 18 during the predetermined time period. Any other number of predetermined actions may be taken to determine whether or not the patient was within the predetermined vicinity of the medical facility during the predetermined time period, as understood by those skilled in the art.

Referring now additionally to FIGS. 24-29, additional method aspects according to an embodiment of the present invention are now described in greater detail. These method aspects are directed to preventing medical claim fraud by comparing historical location data of a patient locating device to determine if the patient locating device was within a predetermined vicinity of a medical facility during a predetermined time period. Referring now more specifically to the flowchart 360 illustrated in FIG. 24, additional details of the method aspect of an embodiment of the present invention is now described in greater detail. From the start (Block 362), it is determined if the predetermined event has occurred at Block 364. If it is determined at Block 364 that the predetermined event has not occurred, then the method awaits occurrence of the predetermined event at the start Block 362. If, however, it is determined at Block 364 that the predetermined event has occurred, then a first signal is transmitted from the first controller to the second controller at Block 366. At Block 368, historical location data of the patient locating device is retrieved from the data center. At Block 370, it is determined whether or not the historical location data indicates that the patient locating device was within the predetermined vicinity of the medical facility during the predetermined time period.

If it is determined at Block 370 that the historical location data indicates that the patient locating device was within the vicinity of the medical facility during the predetermined time period, then an indication is transmitted from the second controller to the first controller that the patient locating device was within the predetermined vicinity during the predetermined time period at Block 372 (wherein the predetermined time period is presumably an indication of the time period during which medical services were provided to the patient). If, however, it is determined at Block 370 that the historical location data does not indicate that the patient locating device was within the predetermined vicinity of the medical facility during the predetermined time period, then an indication is transmitted from the second controller to the first controller that the patient locating device was not within the predetermined vicinity during the predetermined time period at Block 374. The method is ended at Block 376.

Figure 25:
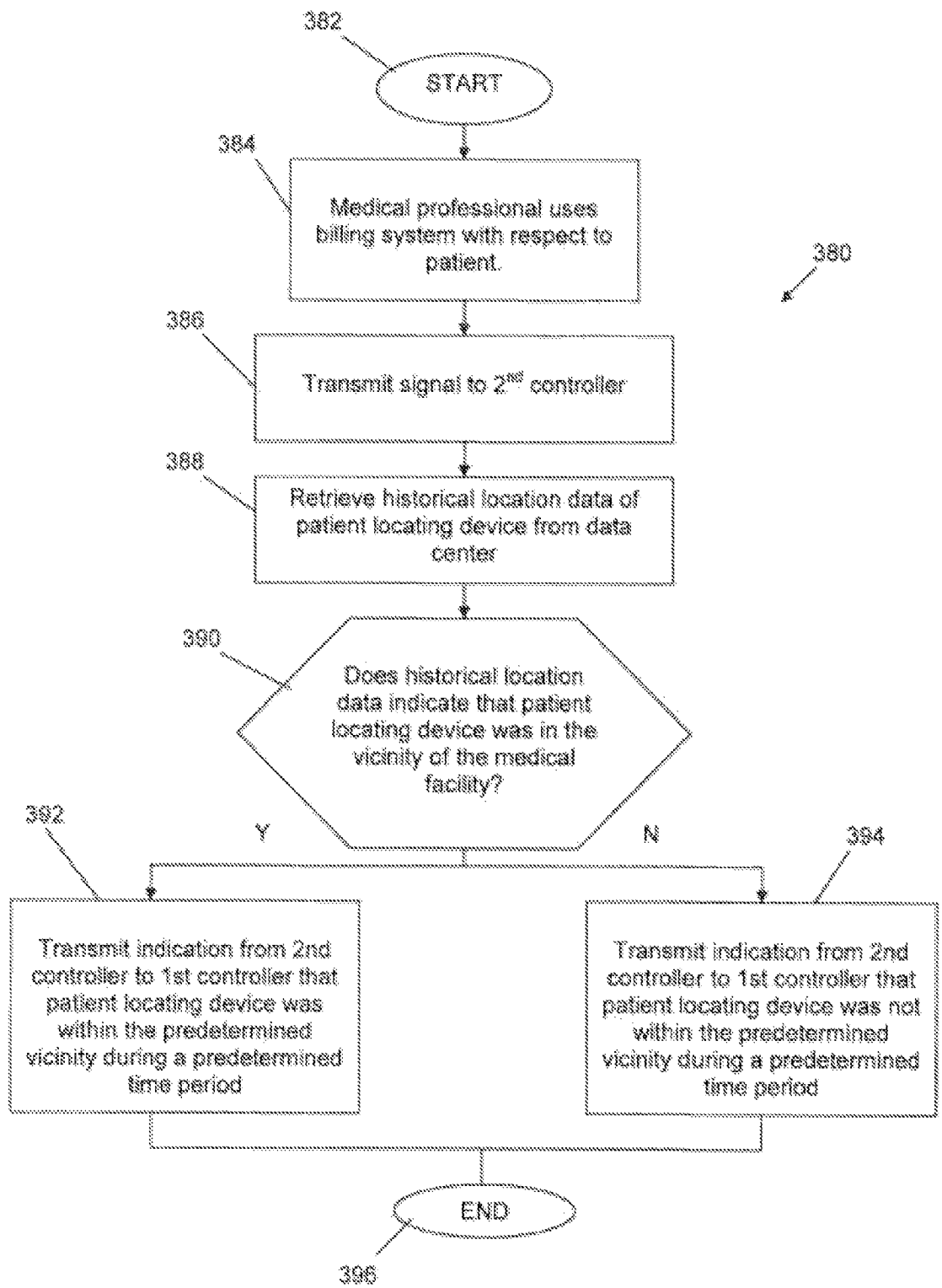

Referring now additionally to the flowchart 380 illustrated in FIG. 25, yet another method aspect according to an embodiment of the present invention is now described in greater detail. The method illustrated in the flowchart 380 of FIG. 25 provides that the predetermined event that occurs to prompt retrieval of historical location data of the patient locating device is use of the billing system with respect to the patient. More specifically, from the start (Block 382), the medical professional may use the billing system with respect to the patient at Block 384. Upon use of the billing system at Block 384, the first signal is transmitted from the first controller to the second controller at Block 386, and historical location data of the patient locating device may be retrieved from the data center at Block 388

At Block 390, it is determined whether or not the historical location date that was retrieved from the data center indicates that the patient locating device was within the predetermined vicinity of the medical facility during the predetermined time period (wherein the predetermined time period is presumably an indication of the time period during which medical services were provided to the patient). If it is determined at Block 390 that the patient locating device was within the predetermined vicinity of the medical facility during the predetermined time period, then an indication is transmitted from the second controller to the first controller that the patient locating device was within the predetermined vicinity during the predetermined time period at Block 392. If, however, it is determined at Block 390 that the patient locating device was not within the predetermined vicinity of the medical facility during the predetermined time period, then an indication is transmitted from the second controller to the first controller that the patient locating device was not within the predetermined vicinity during the predetermined time period at Block 394. The method is ended at Block 396.

Figure 26:
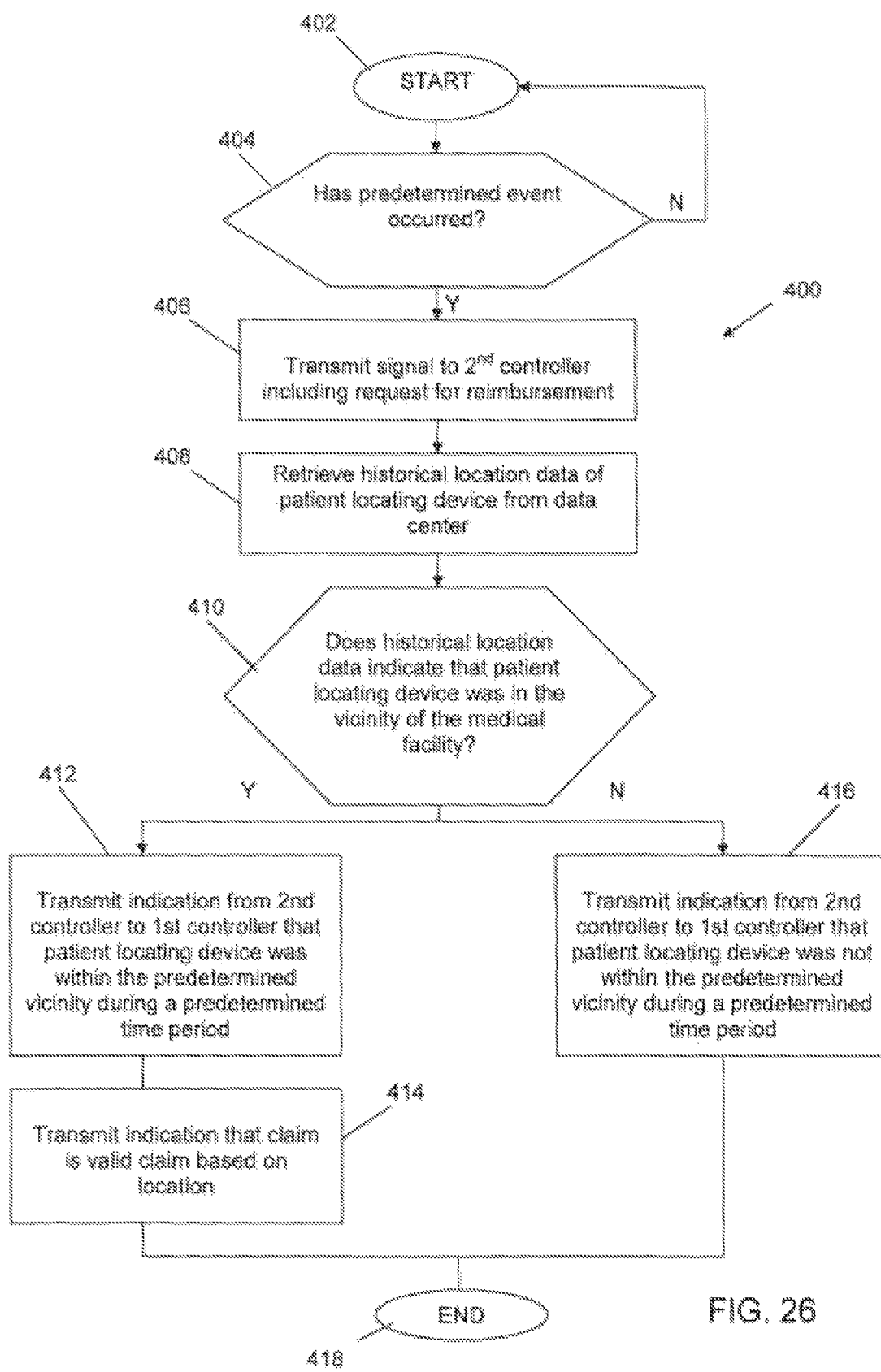

Referring now additionally to the flowchart 400 illustrated in FIG. 26, another method aspect of an embodiment of the present invention is now described in greater detail. More specifically, from the start (Block 402), it is determined at Block 404 whether or not the predetermined event has occurred. If it is determined at Block 404 that the predetermined event has not occurred, then the method awaits occurrence of the predetermined event at the start Block 402. If, however, if is determined at Block 404 that the predetermined event has occurred, then a first signal is transmitted from the first controller to the second controller at Block 406, and historical location data of the patient locating device is retrieved from a data center at Block 408. The first signal may also include information relating to a request for reimbursement of medical expenses for medical services that were provided to the patient.

At Block 410, it is determined whether or not the historical location data retrieved from the data center indicates that the patient locating device was within the predetermined vicinity of the medical facility during the predetermined time period (wherein the predetermined time period is presumably an indication of the time period during which medical services were provided to the patient). If it is determined at Block 410 that the patient locating device was within the predetermined vicinity of the medical facility during the predetermined time period, then an indication is transmitted from the second controller to the first controller that the patient locating device was within the predetermined vicinity during the predetermined time period at Block 412. Along with this indication, the signal may include an indication that the claim is a valid claim based on the location of the patient locating device during the predetermined time period at Block 414. If, however, if is determined at Block 410 that the historical location data does not indicate that the patient locating device was not within the predetermined vicinity of the medical facility during the predetermined time period, than an indication is transmitted from the second controller to the first controller that the patient locating device was not within the predetermined vicinity during the predetermined time period at Block 416. Thereafter, the method is ended at Block 418.

Figure 27:
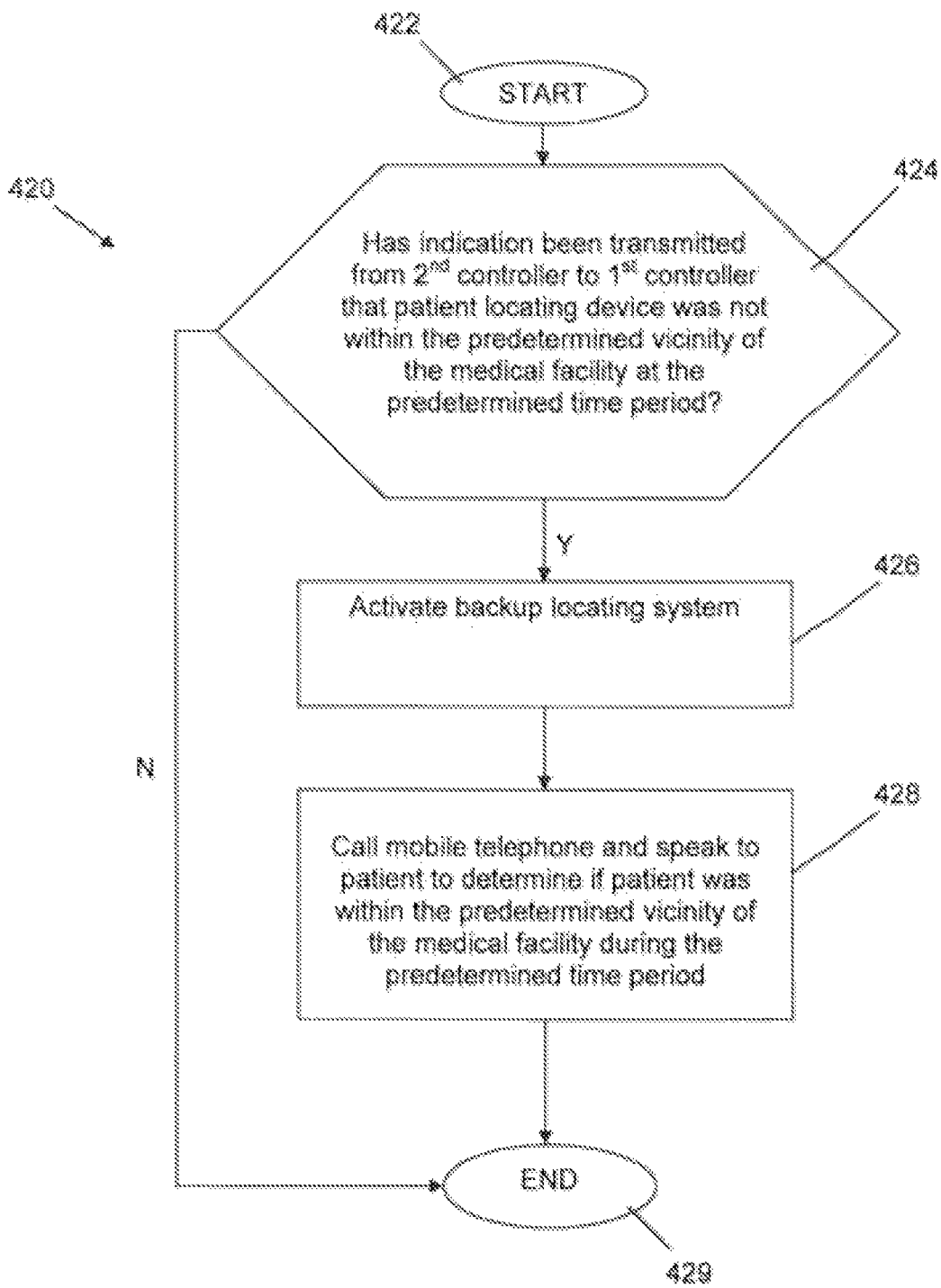
Figure 28:
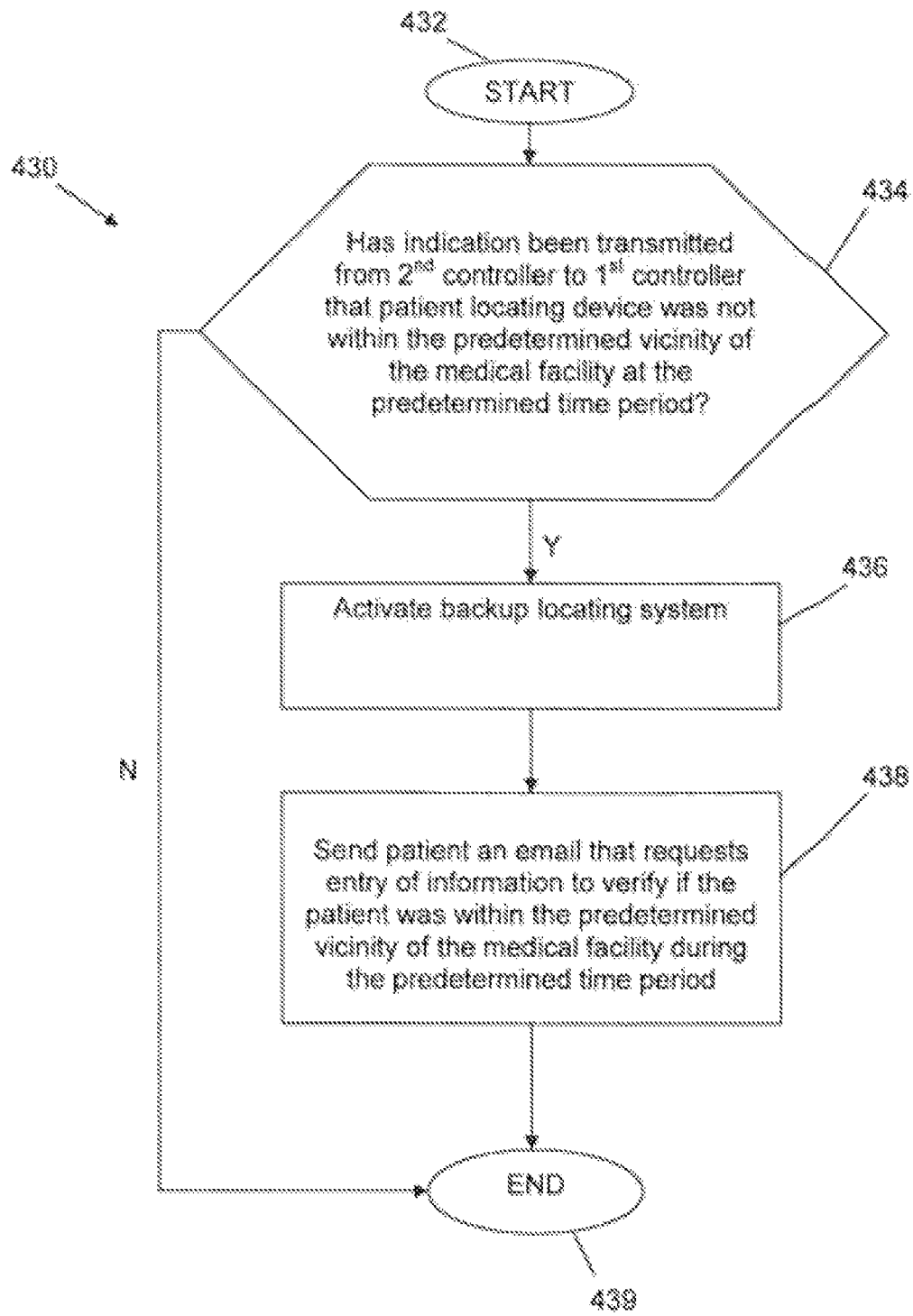
Figure 29:
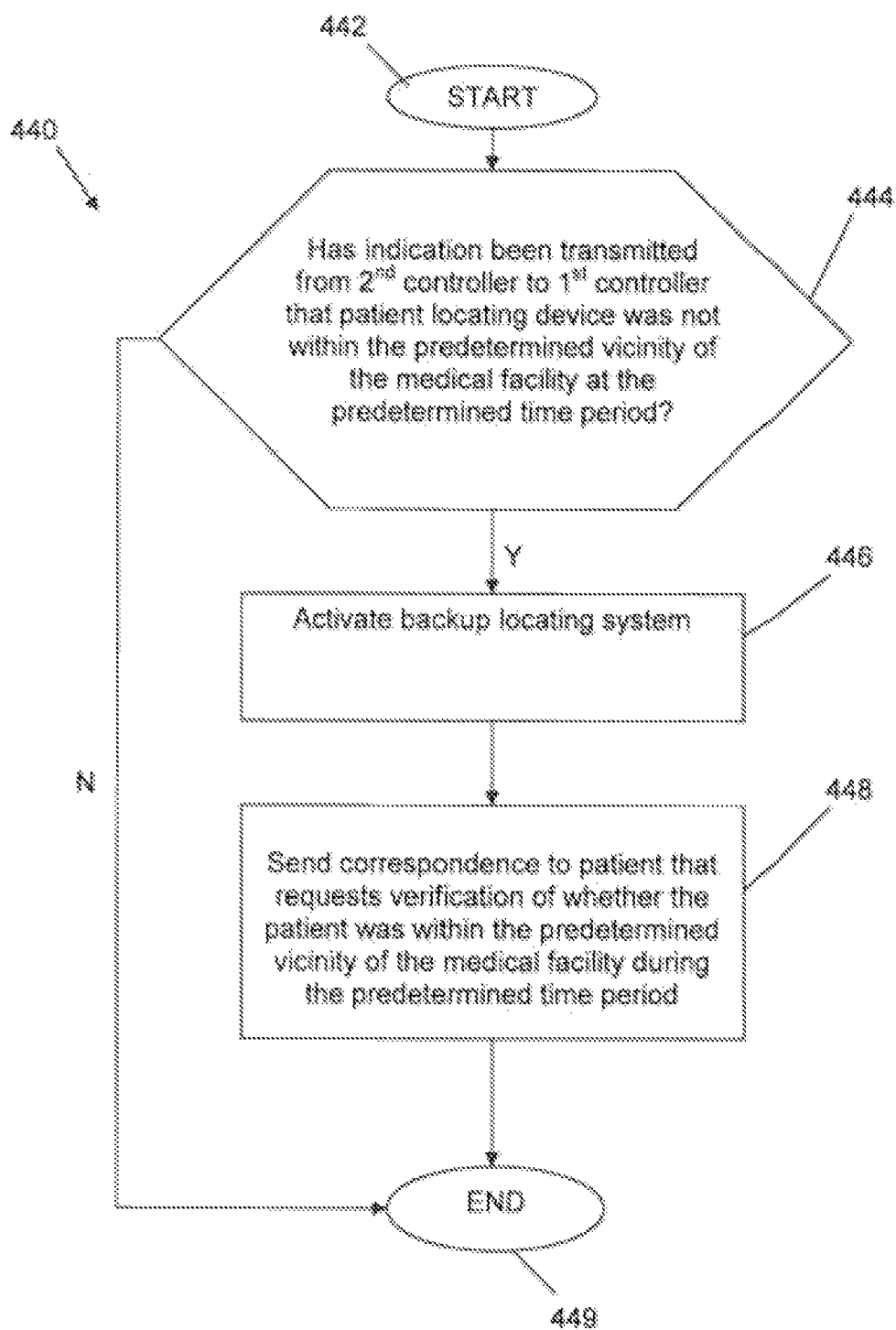

Referring now additionally to FIGS. 27, 28 and 29, backup locating systems for use in situations where an indication has been transmitted from the second controller to the first controller that the patient locating device was not within the predetermined vicinity of the medical facility at the predetermined time period are now described in greater detail (wherein the predetermined time period is presumably an indication of the time period during which medical services were provided to the patient). More specifically, and referring to the flowchart 420 illustrated in FIG. 27, from the start (Block 422), if it is determined at Block 424 that an indication has not been transmitted from the second controller to the first controller that the patient locating device was not within the predetermined vicinity of the medical facility during the predetermined time period, then the method is simply ended at Block 429. If, however, an indication has been transmitted from the second controller to the first controller that the patient locating device was not within the predetermined vicinity of the medical facility at the predetermined time period at Block 424, then the backup locating system may be activated Block 426, and the mobile telephone of the patient may be called at Block 428. Upon calling the mobile telephone of the patient at Block 428, the patient may be spoken to in order to determine if the patient was within the predetermined vicinity of the medical facility during the predetermined time period. The method is thereafter ended at Block 429.

The flowchart 430 illustrated in FIG. 28 provides a method for preventing medical claim fraud including a backup locating system that carries out a different action then that which was illustrated in FIG. 27. More specifically, from the start (Block 432), if it is determined at Block 434 that an indication has been transmitted from the second controller to the first controller that the patient locating device was not within the predetermined vicinity off the medical facility at the predetermined time period, then the backup locating system is activated at Block 436 and the patient is sent an email that requests entry of information to verify if the patient was within the predetermined vicinity of the medical facility during the predetermined time period at Block 438. Thereafter, the method is ended at Block 439.

Referring now additionally to the flowchart 440 illustrated in FIG. 29, another method aspect according to an embodiment of the present invention is now described in which the action taken by the backup locating system is different than those described in FIGS. 27 and 28. More particularly, from the start (Block 442), if it is determined at Block 444 that an indication has been transmitted from the second controller to the first controller that the patient locating device was not within the predetermined vicinity of the medical facility at the predetermined time period, then the backup locating system is activated at Block 446, and correspondence is sent to the patient that requests verification of whether the patient was within the predetermined vicinity of the medical facility during the predetermined time period at Block 448. Thereafter the method is ended at Block 449.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medical claim fraud prevention system comprising:
   a first controller positioned at a medical facility;
   a second controller positioned at a patient information collection center and adapted to be in communication with a data center having historical location information relating to a patient locating device associated with a patient; and
   a medical software system adapted to be in communication with the first controller;
   wherein the medical software system is configured to prompt a user to enter medical information related to the patient, the medical information comprising at least one of medical observations, diagnoses, medical conditions, previous medical treatments, and prescriptions;
   wherein the medical software system is configured to send medical information related to the patient to the first controller;
   wherein the first controller is configured to send a signal requesting a historical location of the patient locating device to the second controller responsive to the medical information received from the medical software system; and
   wherein the second controller is configured to transmit an indication to the first controller in response to the signal received from the first controller regarding the historical location of the patient locating device and whether the patient locating device was within a vicinity of the medical facility during a time period.

2. A system according to claim 1 wherein the medical software system is at least one of a billing system and a patient information collection system.

3. A system according to claim 1 wherein the patient locating device is a GPS enabled mobile telephone.

4. A system according to claim 1 wherein the patient locating device is a signal transmitting device capable of being triangulated to determine location data.

5. A system according to claim 1 wherein the medical facility is at least one of a doctor's office, a hospital, a pharmacy, a therapy center, a medical laboratory, a medical clinic, a rehabilitation facility, a dialysis unit, an outpatient center, an assisted care living facility, an emergency room and a nursing home.

6. A system according to claim 1 wherein the patient information collection center is associated with processing health insurance claims.

7. A system according to claim 1 wherein the signal transmitted from the first controller to the second controller includes information relating to a claim for reimbursement relating to medical services being provided to the patient at the medical facility.

8. A system according to claim 7 wherein the second controller transmits a signal to the first controller including an indication of whether or not the claim is a valid claim based on the indication of whether the patient locating device was within the vicinity of the medical facility during the time period.

9. A system according to claim 1 further comprising a backup locating system that is activated to perform an action based on a backup event.

10. A system according to claim 9 wherein the backup event that activates the backup locating system is an indication received from the second controller that the patient locating device was not within the vicinity of the medical facility during the time period.

11. A system according to claim 9 wherein the patient locating device is a mobile telephone; and wherein the action is calling the mobile telephone and speaking with the patient to determine if the patient was within the vicinity of the medical facility during the time period.

12. A system according to claim 9 wherein the action is sending the patient an email that requests entry of information to verify if the patient was within the vicinity of the medical facility during the time period.

13. A system according to claim 9 wherein the action is sending correspondence to the patient that requests verification of whether the patient was within the vicinity of the medical facility during the time period.

14. A method of preventing medical claim fraud, the method comprising:
   prompting a user to enter medical information related to a patient into a medical software system positioned at a medical facility, the medical information comprising at least one of medical observations, diagnoses, medical conditions, previous medical treatments, and prescriptions;
   transmitting the medical information related to the patient from the medical software system to a first controller positioned at the medical facility and in communication with the medical software system;
   transmitting a signal requesting a historical location of a patient locating device associated with the patient from the first controller to a second controller positioned at a patient information collection center responsive to receiving the medical information related to the patient from the medical software system, wherein the second controller is adapted to be in communication with a data center having historical location information relating to the patient locating device; and
   transmitting an indication from the second controller to the fist controller responsive to the signal received from the first controller requesting the historical location of the patient locating device and indicating whether the patient locating device was within a vicinity of the medical facility during a time period.

15. A method according to claim 14 wherein the medical software system is at least one of a billing system and a patient information collection system.

16. A method according to claim 14 wherein the patient locating device is a GPS enabled mobile telephone.

17. A method according to claim 14 wherein the patient locating device is a signal transmitting device capable of being triangulated to determine location data.

18. A method according to claim 14 wherein the medical facility is at least one of a doctor's office, a hospital, a pharmacy, a therapy center, a medical laboratory, a medical clinic, a rehabilitation facility, a dialysis unit, an outpatient center, an assisted care living facility, an emergency room and a nursing home.

19. A method according to claim 14 wherein the patient information collection center is associated with processing health insurance claims.

20. A method according to claim 14 wherein the signal transmitted from the first controller to the second controller includes information relating to a claim for reimbursement relating to medical services being provided to the patient at the medical facility.

21. A method according to claim 20 wherein the second controller transmits a signal to the first controller including an indication of whether or not the claim is a valid claim based on the indication of whether the patient locating device was within the vicinity of the medical facility during the time period.

22. A method according to claim 14 further comprising activating a backup locating system to perform an action based on a backup event.

23. A method according to claim 22 wherein the backup event that activates the backup locating system is an indication received from the second controller that the patient locating device was not within the vicinity of the medical facility during the time period.

24. A method according to claim 22 wherein the patient locating device is a mobile telephone; and wherein the action is calling the mobile telephone and speaking with the patient to determine if the patient was within the vicinity of the medical facility during the time period.

25. A method according to claim 22 wherein the action is sending the patient an email that requests entry of information to verify if the patient was within the vicinity of the medical facility during the time period.

26. A method according to claim 22 wherein the action is sending correspondence to the patient that requests verification of whether the patient was within the vicinity of the medical facility during the time period.

* * * * *